United States Patent
Luther et al.

(10) Patent No.: US 11,622,950 B2
(45) Date of Patent: Apr. 11, 2023

(54) THERAPEUTIC METHODS AND COMPOSITIONS FOR TREATING PANCREATIC CANCER USING 6,8-BIS-BENZYLTHIO-OCTANOIC ACID

(71) Applicant: Rafael Pharmaceuticals, Inc., Cranbury, NJ (US)

(72) Inventors: Sanjeev Luther, Cranbury, NJ (US); Robert G. L. Shorr, Edison, NJ (US)

(73) Assignee: Cornerstone Pharmaceuticals, Inc., Cranbury, NJ (US)

( * ) Notice: Subject to any disclaimer, the term of this patent is extended or adjusted under 35 U.S.C. 154(b) by 0 days.

(21) Appl. No.: 17/261,237

(22) PCT Filed: Jul. 23, 2019

(86) PCT No.: PCT/US2019/042919
§ 371 (c)(1),
(2) Date: Jan. 19, 2021

(87) PCT Pub. No.: WO2020/023439
PCT Pub. Date: Jan. 30, 2020

(65) Prior Publication Data
US 2021/0267922 A1    Sep. 2, 2021

Related U.S. Application Data

(60) Provisional application No. 62/834,470, filed on Apr. 16, 2019, provisional application No. 62/782,938, filed on Dec. 20, 2018, provisional application No. 62/701,993, filed on Jul. 23, 2018.

(51) Int. Cl.
| | | |
|---|---|---|
| A61K 31/192 | (2006.01) | |
| A61P 35/00 | (2006.01) | |
| A61K 9/00 | (2006.01) | |
| A61K 31/337 | (2006.01) | |
| A61K 31/7068 | (2006.01) | |

(52) U.S. Cl.
CPC .......... *A61K 31/192* (2013.01); *A61K 9/0053* (2013.01); *A61K 31/337* (2013.01); *A61K 31/7068* (2013.01); *A61P 35/00* (2018.01)

(58) Field of Classification Search
CPC ................ A61K 31/192; A61K 31/337; A61K 31/7068; A61P 35/00
See application file for complete search history.

(56) References Cited

PUBLICATIONS

NCT03435289 (A Study of CPI-613 With Gemcitabine and Nab-paclitaxel for Patients With Advanced or Metastatic Pancreatic Cancer; Feb. 2018).*

* cited by examiner

*Primary Examiner* — Pancham Bakshi
(74) *Attorney, Agent, or Firm* — Todd Spradau

(57) ABSTRACT

The invention provides methods, compositions, and medical kits for treating pancreatic cancer using (i) 6,8-bis(benzylsulfanyl)octanoic acid or a pharmaceutically acceptable salt thereof in combination with (ii) gemcitabine or a pharmaceutically acceptable salt thereof, and (iii) nab-paclitaxel.

10 Claims, 3 Drawing Sheets

THERAPEUTIC METHODS AND COMPOSITIONS FOR TREATING PANCREATIC CANCER USING 6,8-BIS-BENZYLTHIO-OCTANOIC ACID

CROSS-REFERENCE TO RELATED APPLICATIONS

This application is the national stage of International (PCT) Patent Application Serial No. PCT/US2019/042919, filed Jul. 23, 2019, which claims the benefit of and priority to U.S. Provisional Patent Application Ser. No. 62/701,993, filed Jul. 23, 2018; U.S. Provisional Patent Application Ser. No. 62/782,938 filed Dec. 20, 2018; and U.S. Provisional Patent Application Ser. No. 62/834,470, filed Apr. 16, 2019; the contents of each application are hereby incorporated by reference.

FIELD OF THE INVENTION

The invention provides methods, compositions, and medical kits for treating pancreatic cancer using (i) 6,8-bis(benzylsulfanyl)octanoic acid or a pharmaceutically acceptable salt thereof in combination with (ii) gemcitabine or a pharmaceutically acceptable salt thereof, and (iii) nab-paclitaxel.

BACKGROUND

Cancer is a leading cause of death in many industrialized countries. Significant advances have been made in improving the diagnosis and treatment of cancer. However, current treatment options often suffer from severe adverse side effects and/or the treatments are not effective for all patients. For example, many clinically-accepted chemotherapeutic agents can induce profound damage to normal, proliferative host cells. Another problem associated with many chemotherapeutic treatments is that, in many tumor types, there is either inherent or acquired resistance to the therapy.

Pancreatic cancer affects a substantial portion of patients that suffer from cancer. Exemplary therapies currently used to help treat patients suffering from pancreatic cancer include surgery, radiation therapy, and chemotherapy. Surgery involves surgical removal of pancreatic tissue afflicted with cancer. Radiation therapy involves applying ionizing radiation to the diseased area of the pancreas. However, not all patients achieve sufficient remission of pancreatic cancer using existing therapies and/or experience adverse side effects when subjected to existing therapies.

Accordingly, the need exists for new therapeutic methods that provide improved efficacy and/or reduced side effects for treating pancreatic cancer. The present invention addresses this need and provides other related advantages.

SUMMARY

The invention provides methods, compositions, and medical kits for treating pancreatic cancer using (i) 6,8-bis(benzylsulfanyl)octanoic acid or a pharmaceutically acceptable salt thereof in combination with (ii) gemcitabine or a pharmaceutically acceptable salt thereof, and (iii) nab-paclitaxel. The pancreatic cancer may be, for example, characterized as metastatic. The 6,8-bis(benzylsulfanyl)octanoic acid or a pharmaceutically acceptable salt thereof may be formulated as a pharmaceutical composition, such as a pharmaceutical composition containing an ion pairing agent. The 6,8-bis(benzylsulfanyl)octanoic acid or a pharmaceutically acceptable salt thereof may be formulated as a pharmaceutical composition for administration to the patient separate from a pharmaceutical composition containing other agent(s) used in the combination therapy, such as gemcitabine or a pharmaceutically acceptable salt thereof.

Accordingly, one aspect of the invention provides a method for treating pancreatic cancer. The method comprises administering to a patient in need thereof a therapeutically effective amount of (i) a first therapeutic agent comprising 6,8-bis(benzylsulfanyl)octanoic acid or a pharmaceutically acceptable salt thereof, (ii) a second therapeutic agent comprising gemcitabine or a pharmaceutically acceptable salt thereof, and (iii) a third therapeutic agent comprising nab-paclitaxel, in order to treat the pancreatic cancer. The first therapeutic agent, second therapeutic agent, and/or third therapeutic agent may be administered, for example, by intravenous administration. Desirably, the first therapeutic agent, second therapeutic agent, and third therapeutic agent are administered to the patient all on the same day.

Another aspect of the invention provides a medical kit for treating pancreatic cancer. The medical kit may comprise (i) a first therapeutic agent comprising 6,8-bis(benzylsulfanyl)octanoic acid or a pharmaceutically acceptable salt thereof, and (ii) instructions for treating pancreatic cancer in a patient using the first therapeutic agent in combination with (a) a second therapeutic agent comprising gemcitabine or a pharmaceutically acceptable salt thereof and (b) a third therapeutic agent comprising nab-paclitaxel. The instructions may specify, for example, the route of administration for the first therapeutic agent, the second therapeutic agent, and/or the third therapeutic agent, such as by intravenous administration.

The foregoing aspects of the invention are described in more detail, along with additional embodiments, in the detailed description below.

DETAILED DESCRIPTION

Figure 1:
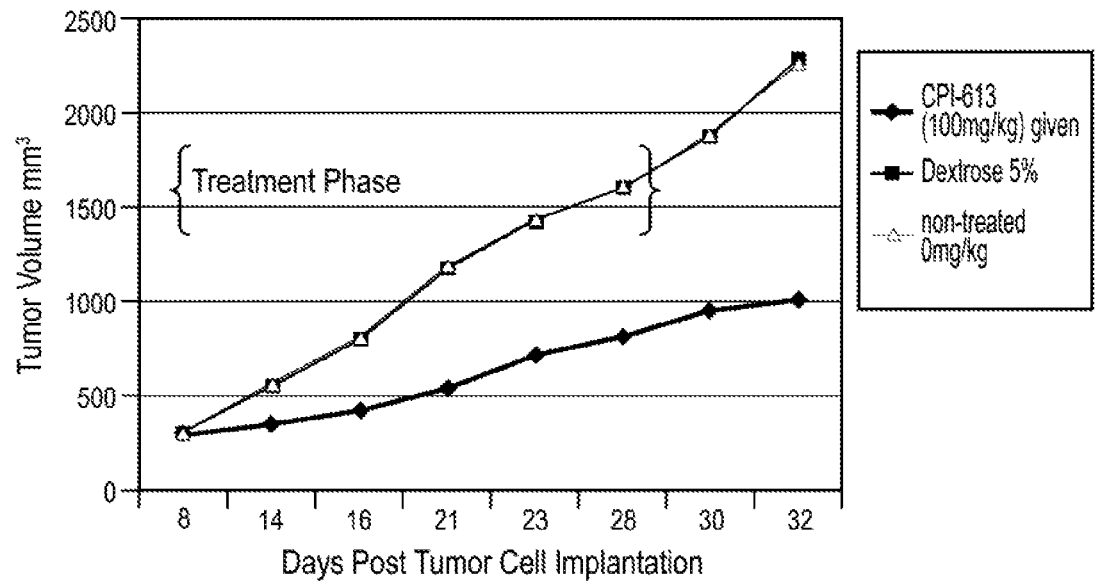
FIG. 1 depicts the anti-tumor efficacy of oral 6,8-bis(benzylsulfanyl)octanoic acid in human non-small cell lung cancer xenografts in mice.
Figure 1:
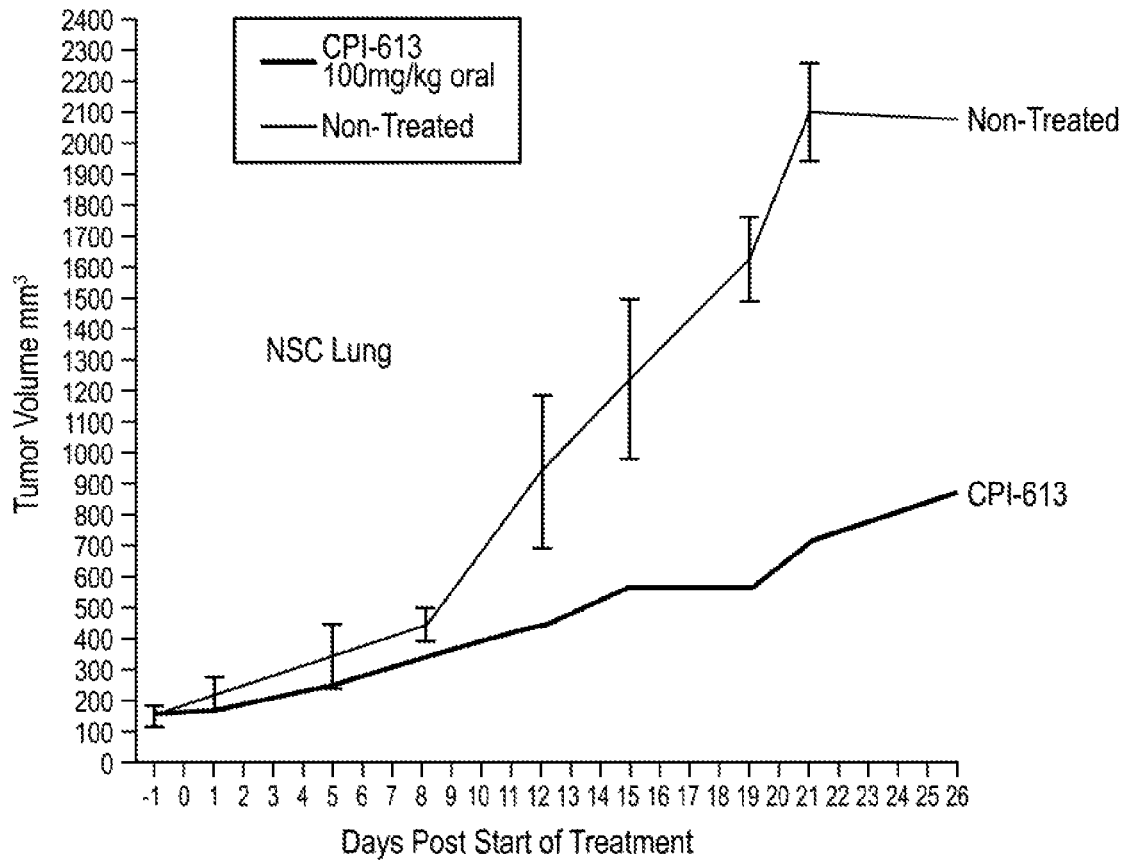

The invention provides methods, compositions, and medical kits for treating pancreatic cancer using (i) 6,8-bis(benzylsulfanyl)octanoic acid or a pharmaceutically acceptable salt thereof in combination with (ii) gemcitabine or a pharmaceutically acceptable salt thereof, and (iii) nab-paclitaxel. The pancreatic cancer may be, for example, characterized as metastatic. The 6,8-bis(benzylsulfanyl)octanoic acid or a pharmaceutically acceptable salt thereof may be formulated as a pharmaceutical composition, such as a pharmaceutical composition containing an ion pairing agent. The 6,8-bis(benzylsulfanyl)octanoic acid or a pharmaceutically acceptable salt thereof may be formulated as a pharmaceutical composition for administration to the patient separate from a pharmaceutical composition containing other agent(s) used in the combination therapy, such as gemcitabine or a pharmaceutically acceptable salt thereof. The practice of the present invention employs, unless otherwise indicated, conventional techniques of organic chemistry, pharmacology, and biochemistry. Such techniques are explained in the literature, such as "Comprehensive Organic Synthesis" (B. M. Trost & I. Fleming, eds., 1991-1992); which is incorporated by reference. Various aspects of the invention are set forth below in sections; however, aspects of the invention described in one particular section are not to be limited to any particular section.

I. DEFINITIONS

To facilitate an understanding of the present invention, a number of terms and phrases are defined below.

The terms "a," "an" and "the" as used herein mean "one or more" and include the plural unless the context is inappropriate The term "6,8-bis(benzylsulfanyl)octanoic acid" refers to CPI-613, i.e., the compound having the chemical structure

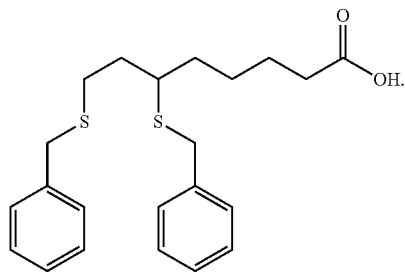 [SMILES: O=C(O)CCCCC(CCSCc1ccccc1)SCc1ccccc1]

Certain compounds contained in compositions of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention.

As used herein, the term "patient" refers to organisms to be treated by the methods of the present invention. Such organisms preferably include, but are not limited to, mammals (e.g., murines, simians, equines (horses), bovines (cattle), porcines, canines, felines, and the like), and most preferably includes humans.

As used herein, the term "treating" includes any effect, e.g., lessening, reducing, modulating, ameliorating or eliminating, that results in the improvement of the condition, disease, disorder, and the like, or ameliorating a symptom thereof. For example, treatment can include diminishment of a symptom of a disorder or complete eradication of a disorder. As another example, treatment can include slowing the progression of a disease, or preventing or delaying its recurrence, such as maintenance treatment to prevent or delay relapse.

As used herein, the term "pharmaceutical composition" refers to the combination of an active agent with a carrier, inert or active, making the composition especially suitable for diagnostic or therapeutic use in vivo or ex vivo.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable carrier" refers to any of the standard pharmaceutical carriers. The compositions also can include stabilizers and preservatives. For examples of carriers, stabilizers, and adjuvants, see e.g., Martin, Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present invention which, upon administration to a subject, is capable of providing a compound of this invention. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts. Examples of bases include, but are not limited to, alkali metals (e.g., sodium) hydroxides, alkaline earth metals (e.g., magnesium), hydroxides, ammonia, and compounds of formula $NW_3$, wherein W is $C_{1-4}$ alkyl, and the like.

Further examples of salts include salts made using the ion pairing agents described in U.S. Pat. No. 8,263,653, the entire disclosure of which is incorporated by reference herein. Still further ion pairing agents can be selected with guidance from Handbook of Pharmaceutical Salts Properties, Selection and Use, IUPAC, Wiley-VCH, P. H. Stahl, ed., the entire disclosure of which is incorporated by reference herein.

Further examples of salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Still other examples of salts include anions of the compounds of the present invention compounded with a suitable cation such as $Na^+$, $NH_4^+$, and $NW_4^+$ (wherein W is a $C_{1-4}$ alkyl group), and the like. The term "alkyl" is art-recognized, and includes saturated aliphatic groups, including straight-chain alkyl groups and branched-chain alkyl groups.

In certain embodiments, the pharmaceutically acceptable salts are those prepared from the following acids: hydrochloric, hydrobromic, sulfuric, nitric, phosphoric, maleic, acetic, palicylic, p-toluene sulfonic, tartaric, citric, methane sulfonic, formic, malonic, succinic, naphthalene-2-sulfonic, and benzene sulfonic. In certain other embodiments, the pharmaceutically acceptable salts are alkaline metal or alkaline earth salts, such as sodium, potassium or calcium salts of a carboxylic acid group.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

II. THERAPEUTIC APPLICATIONS

The invention provides methods for treating pancreatic cancer using (i) 6,8-bis(benzylsulfanyl)octanoic acid or a pharmaceutically acceptable salt thereof in combination with (ii) gemcitabine or a pharmaceutically acceptable salt thereof, and (iii) nab-paclitaxel. The methods are described in more detail below.

One aspect of the invention provides a method for treating pancreatic cancer. The method comprises administering to a patient in need thereof a therapeutically effective amount of (i) a first therapeutic agent comprising 6,8-bis(benzylsulfanyl)octanoic acid or a pharmaceutically acceptable salt thereof, (ii) a second therapeutic agent comprising gemcitabine or a pharmaceutically acceptable salt thereof, and (iii) a third therapeutic agent comprising nab-paclitaxel, in order to treat the pancreatic cancer. The method may be further characterized according to one or more features described herein below.

Type of Pancreatic Cancer

The method may be further characterized according to the type of pancreatic cancer. In certain embodiments, the pancreatic cancer is metastatic pancreatic cancer. In certain other embodiments, the pancreatic cancer is locally advanced. In certain other embodiments, the pancreatic cancer is histologically or cytologically documented and measurable locally advanced pancreatic adenocarcinoma. In certain other embodiments, the pancreatic cancer is histologically or cytologically documented and measurable metastatic pancreatic adenocarcinoma. In certain embodiments, the pancreatic cancer is previously untreated. In certain embodiments, the pancreatic cancer is previously untreated with systemic therapies. In certain embodiments, the pancreatic cancer is previously untreated with systemic therapies or local treatment with chemoradiation. In certain other embodiments, the pancreatic cancer is histologically or cytologically documented and measurable locally advanced pancreatic adenocarcinoma that is previously untreated. In certain other embodiments, the pancreatic cancer is histologically or cytologically documented and measurable metastatic pancreatic adenocarcinoma that is previously untreated. In certain other embodiments, the pancreatic cancer is histologically or cytologically documented and measurable locally advanced pancreatic adenocarcinoma that is previously untreated with systemic therapies. In certain other embodiments, the pancreatic cancer is histologically or cytologically documented and measurable metastatic pancreatic adenocarcinoma that is previously untreated with systemic therapies. In certain other embodiments, the pancreatic cancer is histologically or cytologically documented and measurable locally advanced pancreatic adenocarcinoma that is previously untreated with systemic therapies or local treatment with chemoradiation. In certain other embodiments, the pancreatic cancer is histologically or cytologically documented and measurable metastatic pancreatic adenocarcinoma that is previously untreated with systemic therapies or local treatment with chemoradiation.

General Aspects of Administering a Therapeutic Agent to a Patient

Generally, a therapeutic agent, e.g., 6,8-bis(benzylsulfanyl)octanoic acid or a pharmaceutically acceptable salt thereof, is delivered to the patient in a therapeutically effective amount. The therapeutically effective amount of a therapeutic agent may vary with the activity of the specific agent employed; the metabolic stability and length of action of that agent; the species, age, body weight, general health, dietary status, sex and diet of the subject; the mode and time of administration; rate of excretion; drug combination, if any; and extent of presentation and/or severity of the particular condition being treated. The precise dosage can be determined, may involve one or several administrations per day, in whichever order is necessary or desirable, to yield the desired results, and the dosage may be adjusted by the individual practitioner to achieve a desired effect. The treatment may involve one or several administrations on one or more days, and the dosage may be adjusted by the individual practitioner to achieve a desired effect. Preferably, the dosage amount of the agent(s) used should be sufficient to interact primarily with disease cells (e.g., tumor cells), leaving normal cells comparatively unharmed (e.g., essentially unharmed).

The dosage amount may be administered in a single dose or in the form of individual divided doses, such as from one to four or more times per day. In certain embodiments, the daily dosage amount is administered in a single dose. In the event that the response in a subject is insufficient at a certain dose, even higher doses (or effective higher doses by a different, more localized delivery route) may be employed to the extent of patient tolerance.

For combination therapy, components in a combination therapy may be administered in a particular order and/or according to a treatment cycle, such as on the same or different days. For example, in certain embodiments, at least one dose of the first therapeutic agent is administered to the patient prior to administering the second therapeutic agent, such as on an earlier day in a treatment cycle. In certain other embodiments, active components of the combination therapy may be administered on the same day of a treatment cycle, for example being co-administered simultaneously. In certain embodiments, at least one dose of a second therapeutic agent is administered to the patient prior to administering the 6,8-bis(benzylsulfanyl)octanoic acid or a pharmaceutically acceptable salt thereof, such as on an earlier day in a treatment cycle. In certain embodiments, active components of the combination therapy may be co-administered in a predetermined manner, ratio, and/or order of addition so as to comprise a treatment cycle. In certain embodiments, treatment cycles may be repeated in order to maximize benefit to the patient.

In certain embodiments, the first therapeutic agent and the second therapeutic agent are administered to the patient on the same day. In certain embodiments, the first therapeutic agent and the third therapeutic agent are administered to the patient on the same day. In certain embodiments, the first therapeutic agent, second therapeutic agent, and third therapeutic agent are all administered to the patient on the same days of each treatment cycle. In certain embodiments, the first therapeutic agent, second therapeutic agent, and third therapeutic agent are all administered to the patient on the same days of each treatment cycle, and the first therapeutic agent is administered first, the third therapeutic agent is administered at the same time or after the first therapeutic agent, and the second therapeutic agent is administered after the third therapeutic agent.

Identity of the First Therapeutic Agent

The therapeutic method may be further characterized according to the identity of the first therapeutic agent. For example, in certain embodiments, the first therapeutic agent is 6,8-bis(benzylsulfanyl)octanoic acid or a pharmaceutically acceptable salt thereof. In certain other embodiments, the first therapeutic agent is 6,8-bis(benzylsulfanyl)octanoic acid. In certain other embodiments, the first therapeutic agent is a salt of 6,8-bis(benzylsulfanyl)octanoic acid. In certain other embodiments, the first therapeutic agent is 6,8-bis(benzylsulfanyl)octanoic acid in the form of an ion pair with triethanolamine. In certain other embodiments, the first therapeutic agent is a triethanolamine salt of 6,8-bis(benzylsulfanyl)octanoic acid.

The first therapeutic agent may be formulated in a pharmaceutical composition. In certain embodiments, the first therapeutic agent is administered to the patient in the form of a pharmaceutical composition comprising 6,8-bis(benzylsulfanyl)octanoic acid and a pharmaceutically acceptable carrier. In certain other embodiments, the first therapeutic agent is administered to the patient in the form of a pharmaceutical composition comprising 6,8-bis(benzylsulfanyl)octanoic acid and an ion pairing agent. In certain embodiments, the first therapeutic agent is administered to the patient in the form of a pharmaceutical composition comprising 6,8-bis(benzylsulfanyl)octanoic acid and triethanolamine. In certain other embodiments, the pharmaceutical composition further comprises dextrose and water. In certain embodiments, the first therapeutic agent is 6,8-bis(benzylsulfanyl)octanoic acid in the form of an ion pair with triethanolamine.

Exemplary ion pairing agents that may be used include, for example, a tertiary amine (such as triethanolamine), other amines such as diethanolamine, monoethanolamine, meglumine, mefenamic acid and tromethamine, and combinations thereof. In certain embodiments, the ion pairing agent is an organic Bronsted base. In certain other embodiments, the ion pairing agent is an amine compound. In yet other embodiments, the ion pairing agent is a monoalkylamine, dialkylamine, trialkylamine, amino-substituted aliphatic alcohol, hydroxymonoalkylamine, hydroxydialkylamine, hydroxytrialkylamine, amino-substituted heteroaliphatic alcohol, alkyldiamine, substituted alkyldiamine, or optionally substituted heteroaryl group containing at least one ring nitrogen atom.

Additional exemplary ion pairing agents include, for example, polyethyleneimine, polyglutamic acid, ammonia, L-arginine, benethamine benzathine, betaine, calcium hydroxide, choline, deanol, diethanolamine(2,2'-iminobis(ethanol)), diethylamine, 2-(diethylamino)-ethanol, ethanolamine, ethylenediamine, N-methyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, and zinc hydroxide. In certain other embodiments, the ion pairing agent is diisopropanolamine, 3-amino-1-propanol, meglumine, morpholine, pyridine, niacinamide, tris(hydroxymethyl)aminomethane, 2-((2-dimethylamino)ethoxy)ethanol, 2-(dimethylamino)ethanol, 1-(2-hydroxyethyl)pyrrolidine, or ammonium hydroxide. In certain other embodiments, the ion pairing agent is an alkali metal hydroxide or alkaline earth metal hydroxide, such as, for example, cesium hydroxide.

In certain embodiments, the first therapeutic agent has a purity of at least about 50% (w/w). In certain embodiments, the first therapeutic agent has a purity of at least about 60% (w/w). In certain embodiments, the first therapeutic agent has a purity of at least about 70% (w/w). In certain embodiments, the first therapeutic agent has a purity of at least about 80% (w/w). In certain embodiments, the first therapeutic agent has a purity of at least about 90% (w/w). In certain embodiments, the first therapeutic agent has a purity of at least about 95% (w/w). In certain embodiments, the first therapeutic agent has a purity of at least about 96% (w/w). In certain embodiments, the first therapeutic agent has a purity of at least about 97% (w/w). In certain embodiments, the first therapeutic agent has a purity of at least about 98% (w/w). In certain embodiments, the first therapeutic agent has a purity of at least about 99% (w/w).

In certain more specific embodiments, the first therapeutic agent is administered in the form of a pharmaceutical composition comprising 6,8-bis(benzylsulfanyl)octanoic acid and triethanolamine. Such pharmaceutical compositions may be further characterized according to the mole ratio of the triethanolamine to 6,8-bis(benzylsulfanyl)octanoic acid. In certain embodiments, the mole ratio of triethanolamine to 6,8-bis(benzylsulfanyl)octanoic acid is in the range of about 10:1 to about 1:10, about 10:1 to about 5:1, or about 8:1. In certain embodiments, the mole ratio of triethanolamine to 6,8-bis(benzylsulfanyl)octanoic acid is about 8:1.

Exemplary Route of Administration for the First Therapeutic Agent

The therapeutic method may be further characterized according to the route of administration of the first therapeutic agent. For example, in certain embodiments, the first therapeutic agent is administered intravenously to the patient. In certain other embodiments, the first therapeutic agent is administered orally to the patient.

Exemplary Dosing Amounts & Regimens for the First Therapeutic Agent

The therapeutic method may be further characterized according to the dose of the first therapeutic agent administered to the patient. Accordingly, in certain embodiments, the first therapeutic agent is administered to the patient at a dosage ranging from about 100 mg/m$^2$ to about 3000 mg/m$^2$ on any day the first therapeutic agent is administered to the patient. In certain embodiments, the first therapeutic agent is administered to the patient at a dosage ranging from about 200 mg/m$^2$ to about 2500 mg/m$^2$ on any day the first therapeutic agent is administered to the patient. In certain embodiments, the first therapeutic agent is administered to the patient at a dosage ranging from about 250 mg/m$^2$ to about 1500 mg/m$^2$ on any day the first therapeutic agent is administered to the patient. In certain embodiments, the first therapeutic agent is administered to the patient at a dosage ranging from about 250 mg/m$^2$ to about 500 mg/m$^2$ on any day the first therapeutic agent is administered to the patient. In certain embodiments, the first therapeutic agent is administered to the patient at a dosage ranging from about 500 mg/m$^2$ to about 1000 mg/m$^2$ on any day the first therapeutic agent is administered to the patient. In certain embodiments, the first therapeutic agent is administered to the patient at a dosage ranging from about 1000 mg/m$^2$ to about 1500 mg/m$^2$ on any day the first therapeutic agent is administered to the patient. In certain embodiments, the first therapeutic agent is administered to the patient at a dosage of about 100 mg/m$^2$ on any day the first therapeutic agent is administered to the patient. In certain embodiments, the first therapeutic agent is administered to the patient at a dosage of about 200 mg/m$^2$ on any day the first therapeutic agent is administered to the patient. In certain embodiments, the first therapeutic agent is administered to the patient at a dosage of about 250 mg/m$^2$ on any day the first therapeutic agent is administered to the patient. In certain embodiments, the first therapeutic agent is administered to the patient at a dosage of about 300 mg/m$^2$ on any day the first therapeutic agent is administered to the patient. In certain embodiments, the first therapeutic agent is administered to the patient at a dosage of about 400 mg/m$^2$ on any day the first therapeutic agent is administered to the patient. In certain embodiments, the first therapeutic agent is administered to the patient at a dosage of about 500 mg/m$^2$ on any day the first therapeutic agent is administered to the patient. In certain embodiments, the first therapeutic agent is administered to the patient at a dosage of about 1000 mg/m$^2$ on any day the first therapeutic agent is administered to the patient. In certain embodiments, the first therapeutic agent is administered to the patient at a dosage of about 1500 mg/m$^2$ on any day the first therapeutic agent is administered to the patient. In certain embodiments, the first therapeutic agent is administered to the patient at a dosage of about 2000 mg/m$^2$ on any day the first therapeutic agent is administered to the patient. In certain embodiments, the first therapeutic agent is administered to the patient at a dosage of about 2500 mg/m$^2$ on any day the first therapeutic agent is administered to the patient. In certain embodiments, the first therapeutic agent is administered to the patient at a dosage of about 3000 mg/m$^2$ on any day the first therapeutic agent is administered to the patient.

In certain embodiments, the therapeutic method may be characterized according to the dosing regimen used for administering the first therapeutic agent to the patient. Accordingly, in certain embodiments, the first therapeutic agent is administered no more frequently than once per any seven day period. In certain embodiments, the first therapeutic agent is administered once per each seven day period for a duration of at least 3 weeks. In certain embodiments, there is at least seven days between any subsequent administration of the first therapeutic agent to the patient.

In certain embodiments, the first therapeutic agent is administered to the patient on days 1 and 15 of a twenty-eight day cycle. In certain embodiments, the first therapeutic agent is administered to the patient on days 1, 8, and 15 of a twenty-eight day cycle.

In certain embodiments, the first therapeutic agent is administered at a dose of about 100 mg/m$^2$ to about 3000 mg/m$^2$ on days 1 and 15 of a twenty-eight day cycle. In certain embodiments, the first therapeutic agent is administered at a dose of about 100 mg/m$^2$ to about 3000 mg/m$^2$ on days 1, 8, and 15 of a twenty-eight day cycle. In certain embodiments, the first therapeutic agent is administered at a dose of about 200 mg/m$^2$ to about 2500 mg/m$^2$ on days 1 and 15 of a twenty-eight day cycle. In certain embodiments, the first therapeutic agent is administered at a dose of about 200 mg/m$^2$ to about 2500 mg/m$^2$ on days 1, 8, and 15 of a twenty-eight day cycle. In certain embodiments, the first therapeutic agent is administered at a dose of about 250 mg/m$^2$ to about 1500 mg/m$^2$ on days 1 and 15 of a twenty-eight day cycle. In certain embodiments, the first therapeutic agent is administered at a dose of about 250 mg/m$^2$ to about 1500 mg/m$^2$ on days 1, 8, and 15 of a twenty-eight day cycle. In certain embodiments, the first therapeutic agent is administered at a dose of about 100 mg/m$^2$ on days 1 and 15 of a twenty-eight day cycle. In certain embodiments, the first therapeutic agent is administered at a dose of about 100 mg/m$^2$ on days 1, 8, and 15 of a twenty-eight day cycle. In certain embodiments, the first therapeutic agent is administered at a dose of about 200 mg/m$^2$ on days 1 and 15 of a twenty-eight day cycle. In certain embodiments, the first therapeutic agent is administered at a dose of about 200 mg/m$^2$ on days 1, 8, and 15 of a twenty-eight day cycle. In certain embodiments, the first therapeutic agent is administered at a dose of about 250 mg/m$^2$ on days 1 and 15 of a twenty-eight day cycle. In certain embodiments, the first therapeutic agent is administered at a dose of about 250 mg/m$^2$ on days 1, 8, and 15 of a twenty-eight day cycle. In certain embodiments, the first therapeutic agent is administered at a dose of about 300 mg/m$^2$ on days 1 and 15 of a twenty-eight day cycle. In certain embodiments, the first therapeutic agent is administered at a dose of about 300 mg/m$^2$ on days 1, 8, and 15 of a twenty-eight day cycle. In certain embodiments, the first therapeutic agent is administered at a dose of about 400 mg/m$^2$ on days 1 and 15 of a twenty-eight day cycle. In certain embodiments, the first therapeutic agent is administered at a dose of about 400 mg/m$^2$ on days 1, 8, and 15 of a twenty-eight day cycle. In certain embodiments, the first therapeutic agent is administered at a dose of about 500 mg/m$^2$ on days 1 and 15 of a twenty-eight day cycle. In certain embodiments, the first therapeutic agent is administered at a dose of about 500 mg/m$^2$ on days 1, 8, and 15 of a twenty-eight day cycle. In certain embodiments, the first therapeutic agent is administered at a dose of about 1000 mg/m$^2$ on days 1, 8, and 15 of a twenty-eight day cycle. In certain embodiments, the first therapeutic agent is administered at a dose of about 1500 mg/m$^2$ on days 1, 8, and 15 of a twenty-eight day cycle. In certain embodiments, the first therapeutic agent is administered at a dose of about 2000 mg/m$^2$ on days 1 and 15 of a twenty-eight day cycle. In certain embodiments, the first therapeutic agent is administered at a dose of about 2000 mg/m$^2$ on days 1, 8, and 15 of a twenty-eight day cycle. In certain embodiments, the first therapeutic agent is administered at a dose of about 2500 mg/m$^2$ on days 1 and 15 of a twenty-eight day cycle. In certain embodiments, the first therapeutic agent is administered at a dose of about 2500 mg/m$^2$ on days 1, 8, and 15 of a twenty-eight day cycle. In certain embodiments, the first therapeutic agent is administered at a dose of about 3000 mg/m$^2$ on days 1 and 15 of a twenty-eight day cycle. In certain embodiments, the first therapeutic agent is administered at a dose of about 3000 mg/m$^2$ on days 1, 8, and 15 of a twenty-eight day cycle. In certain embodiments, each of the above doses of the first therapeutic agent is administered as a two hour IV infusion. In certain embodiments, the dosing cycle is repeated at least once. In certain embodiments, the method of the present invention comprises treatment with at least 6 cycles. In certain embodiments, the method of the present invention comprises treatment with at least 7 cycles. In certain embodiments, the method of the present invention comprises treatment with at least 10 cycles.

In yet other embodiments, first therapeutic agent is administered in a four week cycle in which the first therapeutic agent is administered once per week during the first three weeks followed by one week off. In certain embodiments, the first therapeutic agent is administered on days 1, 8, and 15 of a four week cycle. In certain embodiments, the first therapeutic agent is administered at a dose of about 250 mg/m$^2$ to about 1500 mg/m$^2$ once per week during the first three weeks followed by one week off. In certain embodiments, the first therapeutic agent is administered at a dose of about 250 mg/m$^2$ to about 1500 mg/m$^2$ on days 1, 8, and 15 of a four week cycle. In certain embodiments, the first therapeutic agent is administered at a dose of about 500 mg/m$^2$ to about 1000 mg/m$^2$ once per week during the first three weeks followed by one week off. In certain embodiments, the first therapeutic agent is administered at a dose of about 500 mg/m$^2$ to about 1000 mg/m$^2$ on days 1, 8, and 15 of a four week cycle. In certain embodiments, the first therapeutic agent is administered at a dose of about 1000 mg/m$^2$ to about 1500 mg/m$^2$ once per week during the first three weeks followed by one week off. In certain embodiments, the first therapeutic agent is administered at a dose of about 1000 mg/m$^2$ to about 1500 mg/m$^2$ on days 1, 8, and 15 of a four week cycle. In certain embodiments, each of the above doses of the first therapeutic agent is administered as a two hour IV infusion. In certain embodiments, the scheduled cycle is repeated at least once. In certain embodiments, the scheduled cycle is repeated at least 2, 3, 4 or 5 times. In certain embodiments, the method of the present invention comprises treatment with at least 6 scheduled cycles.

The first therapeutic agent may be orally administered to the patient. The dose and schedule will vary based on, e.g., the characteristics of the patient's cancer and can be readily determined by those of ordinary skill in the art in view of the guidance provided herein. In certain embodiments, the dose and schedule is adapted based on the doses and schedules used intravenously with 6,8-bis(benzylsulfanyl)octanoic acid or a pharmaceutically acceptable salt thereof, such as those set forth herein. In certain embodiments, the dose is the maximum tolerated dose.

An advantage of oral dosing of the first therapeutic agent is that it permits substantially increased dosing flexibility as compared to IV. In the prior art, 6,8-bis(benzylsulfanyl) octanoic acid is formulated as a 50 mg/mL solution in 1 M (150 mg/mL) aqueous triethanolamine, which is diluted from 50 mg/mL to as low as 4 mg/mL (e.g., 12.5 mg/mL) with sterile 5% dextrose for injection (D5W) prior to administration as an IV infusion over 30-120 minutes via a central venous catheter. Such an infusion is inconvenient for patients and effectively precludes regimens involving frequent and/or prolonged dosing. Since the half-life of the first therapeutic agent after IV dosing is only about 1-2 hours (Pardee, T. S. et al., Clin Cancer Res. 2014, 20, 5255-64), more frequent and/or prolonged dosing could advantageously be used to increase the patient's exposure to the first therapeutic agent.

For example, a possible IV schedule for the treatment of pancreatic cancer involves administering the first, second, and third therapeutic agents on days 1, 8, and 15 of a 28 day cycle. If the first therapeutic agent is administered orally, the second and third therapeutic agents could continue to be administered on days 1, 8, and 15 of a 28 day cycle, but the practitioner would have more flexibility with respect to the first therapeutic agent dose and schedule. The first therapeutic agent could be orally administered in a single daily dose on days 1, 8, and 15 of a 28 day cycle. Alternatively, the first therapeutic agent could be administered in two or more (e.g., three, four, or five) divided doses on days 1, 8, and 15 of a 28 day cycle and/or the first therapeutic agent could be administered on different days of the cycle other than and/or in addition to days 1, 8, and 15, up to and including every day.

Another advantage of oral dosing is that it makes maintenance therapy more feasible. For example, a patient who is treated successfully with first line therapy—with or without the first therapeutic agent—and whose cancer is in partial or complete remission, may be treated orally with the first, second, and third therapeutic agents on a chronic basis in order to delay or prevent recurrence. The maintenance treatment may involve, for example, one, two, three, four, or five doses per day of the first therapeutic agent on a regular basis, such as daily or weekly.

In certain embodiments, the first therapeutic agent is orally administered at a dose of about 1 mg to about 10,000 mg on each day it is administered. The daily dose may be administered in one dose or divided into two or more doses, such as three, four, or five doses. In certain embodiments, the daily dose is about 10 mg to about 7,500 mg. In certain embodiments, the daily dose is about 100 mg to about 5,000 mg. In certain embodiments, the daily dose is about 200 mg to about 4,000 mg. In certain embodiments, the daily dose is about 300 mg to about 3,000 mg. In certain embodiments, the daily dose is about 400 mg to about 2,500 mg. In certain embodiments, the daily dose is about 500 mg to about 2,000 mg. In certain embodiments, the daily dose is about 100 mg, 200 mg, 300 mg, 400 mg, 500 mg, 600 mg, 700 mg, 800 mg, 900 mg, 1,000 mg, 1,250 mg, 1,500 mg, 1,750 mg, 2,000 mg, 2,500 mg, 3,000 mg, 3,500 mg, 4,000 mg, 4,500 mg, 5,000 mg, 6,000 mg, 7,000 mg, 8,000 mg, 9,000 mg, or 10,000 mg.

In certain embodiments, a dosing cycle is repeated at least once. In certain embodiments, the method of the present invention comprises treatment with two cycles or more. In certain embodiments, the method of the present invention comprises treatment with three cycles or more. In certain embodiments, the method of the present invention comprises treatment with four cycles or more. In certain embodiments, the method of the present invention comprises treatment with five cycles or more. In certain embodiments, the method of the present invention comprises treatment with six cycles or more. In certain embodiments, the method of the present invention comprises treatment with seven cycles or more. In certain embodiments, the method of the present invention comprises treatment with eight cycles or more. In certain embodiments, the method of the present invention comprises treatment with nine cycles or more. In certain embodiments, the method of the present invention comprises treatment with ten cycles or more. In certain embodiments, the method of the present invention comprises regular treatment with the first therapeutic agent, including on a daily or weekly basis, for an extended period of time, such as one year, two years, three years, or longer.

Identity of the Second Therapeutic Agent

The therapeutic method may be further characterized according to the identity of the second therapeutic agent. For example, in certain embodiments, the second therapeutic agent is a pharmaceutically acceptable salt of gemcitabine. In certain embodiment, the second therapeutic agent is gemcitabine hydrochloride.

Exemplary Route of Administration for the Second Therapeutic Agent

The therapeutic method may be further characterized according to the route of administration of the second therapeutic agent. For example, in certain embodiments, the second therapeutic agent is administered intravenously to the patient.

Exemplary Dosing Amounts & Regimens for the Second Therapeutic Agent

The therapeutic method may be further characterized according to the dose of the second therapeutic agent administered to the patient. Accordingly, in certain embodiments, the second therapeutic agent is administered to the patient at a dosage ranging from about 650 mg/m$^2$ to about 1000 mg/m$^2$ on any day the second therapeutic agent is administered to the patient. In certain embodiments, the second therapeutic agent is administered to the patient at a dosage ranging from about 650 mg/m$^2$ to about 800 mg/m$^2$ on any day the second therapeutic agent is administered to the patient. In certain embodiments, the second therapeutic agent is administered to the patient at a dosage ranging from about 800 mg/m$^2$ to about 1000 mg/m$^2$ on any day the second therapeutic agent is administered to the patient. In certain embodiments, the second therapeutic agent is administered to the patient at a dosage of about 650 mg/m$^2$ on any day the second therapeutic agent is administered to the patient. In certain embodiments, the second therapeutic agent is administered to the patient at a dosage of about 800 mg/m$^2$ on any day the second therapeutic agent is administered to the patient. In certain embodiments, the second therapeutic agent is administered to the patient at a dosage of about 1000 mg/m$^2$ on any day the second therapeutic agent is administered to the patient.

The therapeutic method may be further characterized according to the dosing regimen used for administering the second therapeutic agent to the patient. Accordingly, in certain embodiments, the second therapeutic agent is administered to the patient no more frequently than once per any seven day period. In certain embodiments, the second therapeutic agent is administered to the patient once per each seven day period for a duration of at least 3 weeks. In certain embodiments, there is at least seven days between any subsequent administration of the second therapeutic agent to the patient.

In certain embodiments, the second therapeutic agent is administered to the patient on days 1 and 15 of a twenty-eight day cycle. In certain embodiments, the second therapeutic agent is administered to the patient on days 1, 8, and 15 of a twenty-eight day cycle.

In certain embodiments, the second therapeutic agent is administered at a dose of about 650 mg/m$^2$ to about 1000 mg/m$^2$ on days 1 and 15 of a twenty-eight day cycle. In certain embodiments, the second therapeutic agent is administered at a dose of about 650 mg/m$^2$ to about 1000 mg/m$^2$ on days 1, 8, and 15 of a twenty-eight day cycle. In certain embodiments, the second therapeutic agent is administered at a dose of about 650 mg/m$^2$ on days 1 and 15 of a twenty-eight day cycle. In certain embodiments, the second therapeutic agent is administered at a dose of about 650 mg/m$^2$ on days 1, 8, and 15 of a twenty-eight day cycle. In certain embodiments, the second therapeutic agent is administered at a dose of about 800 mg/m$^2$ on days 1 and 15 of a twenty-eight day cycle. In certain embodiments, the second therapeutic agent is administered at a dose of about 800 mg/m$^2$ on days 1, 8, and 15 of a twenty-eight day cycle. In certain embodiments, the second therapeutic agent is administered at a dose of about 1000 mg/m$^2$ on days 1 and 15 of a twenty-eight day cycle. In certain embodiments, the second therapeutic agent is administered at a dose of about 1000 on days 1, 8, and 15 of a twenty-eight day cycle. In certain embodiments, each of the above doses of the second therapeutic agent is administered as a 30 minute IV infusion. In certain embodiments, the dosing cycle is repeated at least once. In certain embodiments, the method of the present invention comprises treatment with at least 6 cycles. In certain embodiments, the method of the present invention comprises treatment with at least 7 cycles. In certain embodiments, the method of the present invention comprises treatment with at least 10 cycles.

In yet other embodiments, second therapeutic agent is administered in a four week cycle in which the second therapeutic agent is administered once per week during the first three weeks followed by one week off. In certain embodiments, the second therapeutic agent is administered on days 1, 8, and 15 of a four week cycle. In certain embodiments, the second therapeutic agent is administered at a dose of about 650 mg/m$^2$ to about 1000 mg/m$^2$ once per week during the first three weeks followed by one week off. In certain embodiments, the second therapeutic agent is administered at a dose of about 650 mg/m$^2$ to about 1000 mg/m$^2$ on days 1, 8, and 15 of a four week cycle. In certain embodiments, the second therapeutic agent is administered at a dose of about 650 mg/m$^2$ to about 800 mg/m$^2$ once per week during the first three weeks followed by one week off. In certain embodiments, the second therapeutic agent is administered at a dose of about 650 mg/m$^2$ to about 800 mg/m$^2$ on days 1, 8, and 15 of a four week cycle. In certain embodiments, each of the above doses of the second therapeutic agent is administered as an intravenous infusion. In certain embodiments, the scheduled cycle is repeated at least once. In certain embodiments, the scheduled cycle is repeated at least 2, 3, 4 or 5 times. In certain embodiments, the method of the present invention comprises treatment with at least 6 scheduled cycles.

Identity of the Third Therapeutic Agent

The therapeutic method may be further characterized according to the identity of the third therapeutic agent. For example, in certain embodiments, the third therapeutic agent is nab-paclitaxel.

Exemplary Route of Administration for the Third Therapeutic Agent

The therapeutic method may be further characterized according to the route of administration of the third therapeutic agent. For example, in certain embodiments, the third therapeutic agent is administered intravenously to the patient.

Exemplary Dosing Amounts & Regimens for the Third Therapeutic Agent

The therapeutic method may be further characterized according to the dose of the third therapeutic agent administered to the patient. Accordingly, in certain embodiments, the third therapeutic agent is administered to the patient at a dosage ranging from about 80 mg/m$^2$ to about 125 mg/m$^2$ on any day the third therapeutic agent is administered to the patient. In certain embodiments, the third therapeutic agent is administered to the patient at a dosage ranging from about 80 mg/m$^2$ to about 100 mg/m$^2$ on any day the third therapeutic agent is administered to the patient. In certain embodiments, the third therapeutic agent is administered to the patient at a dosage ranging from about 100 mg/m$^2$ to about 125 mg/m$^2$ on any day the third therapeutic agent is administered to the patient. In certain embodiments, the third therapeutic agent is administered to the patient at a dosage of about 80 mg/m$^2$ on any day the third therapeutic agent is administered to the patient. In certain embodiments, the third therapeutic agent is administered to the patient at a dosage of about 100 mg/m$^2$ on any day the third therapeutic agent is administered to the patient. In certain embodiments, the third therapeutic agent is administered to the patient at a dosage of about 125 mg/m$^2$ on any day the third therapeutic agent is administered to the patient.

In certain embodiments, the therapeutic method may be characterized according to the dosing regimen used for administering the third therapeutic agent to the patient. Accordingly, in certain embodiments, the third therapeutic agent is administered to the patient no more frequently than once per any seven day period. In certain embodiments, the third therapeutic agent is administered to the patient once per each seven day period for a duration of at least 3 weeks. In certain embodiments, there is at least seven days between any subsequent administration of the third therapeutic agent to the patient.

In certain embodiments, the third therapeutic agent is administered to the patient on days 1 and 15 of a twenty-eight day cycle. In certain embodiments, the third therapeutic agent is administered to the patient on days 1, 8, and 15 of a twenty-eight day cycle.

In certain embodiments, the third therapeutic agent is administered at a dose of about 80 mg/m$^2$ to about 125 mg/m$^2$ on days 1 and 15 of a twenty-eight day cycle. In certain embodiments, the third therapeutic agent is administered at a dose of about 80 mg/m$^2$ to about 125 mg/m$^2$ on days 1, 8, and 15 of a twenty-eight day cycle. In certain embodiments, the third therapeutic agent is administered at a dose of about 80 mg/m$^2$ on days 1 and 15 of a twenty-eight day cycle. In certain embodiments, the third therapeutic agent is administered at a dose of about 80 mg/m$^2$ on days 1, 8, and 15 of a twenty-eight day cycle. In certain embodiments, the third therapeutic agent is administered at a dose of about 100 mg/m$^2$ on days 1 and 15 of a twenty-eight day cycle. In certain embodiments, the third therapeutic agent is administered at a dose of about 100 mg/m$^2$ on days 1, 8, and 15 of a twenty-eight day cycle. In certain embodiments, the third therapeutic agent is administered at a dose of about 125 mg/m$^2$ on days 1 and 15 of a twenty-eight day cycle. In certain embodiments, the third therapeutic agent is administered at a dose of about 125 mg/m$^2$ on days 1, 8, and 15 of a twenty-eight day cycle. In certain embodiments, each of the above doses of the third therapeutic agent is administered as a 30 minute IV infusion. In certain embodiments, the dosing cycle is repeated at least once. In certain embodiments, the method of the present invention comprises treatment with at least 6 cycles. In certain embodiments, the method of the present invention comprises treatment with at least 7 cycles. In certain embodiments, the method of the present invention comprises treatment with at least 10 cycles.

In yet other embodiments, third therapeutic agent is administered in a four week cycle in which the third therapeutic agent is administered once per week during the first three weeks followed by one week off. In certain embodiments, the third therapeutic agent is administered on days 1, 8, and 15 of a four week cycle. In certain embodiments, the third therapeutic agent is administered at a dose of about 80 mg/m$^2$ to about 125 mg/m$^2$ once per week during the first three weeks followed by one week off. In certain embodiments, the third therapeutic agent is administered at a dose of about 80 mg/m$^2$ to about 125 mg/m$^2$ on days 1, 8, and 15 of a four week cycle. In certain embodiments, the third therapeutic agent is administered at a dose of about 80 mg/m$^2$ to about 100 mg/m$^2$ once per week during the first three weeks followed by one week off. In certain embodiments, the third therapeutic agent is administered at a dose of about 80 mg/m$^2$ to about 100 mg/m$^2$ on days 1, 8, and 15 of a four week cycle. In certain embodiments, the third therapeutic agent is administered at a dose of about 100 mg/m$^2$ to about 125 mg/m$^2$ once per week during the first three weeks followed by one week off. In certain embodiments, the third therapeutic agent is administered at a dose of about 100 mg/m$^2$ to about 125 mg/m$^2$ on days 1, 8, and 15 of a four week cycle. In certain embodiments, each of the above doses of the third therapeutic agent is administered as an intravenous infusion. In certain embodiments, the scheduled cycle is repeated at least once. In certain embodiments, the scheduled cycle is repeated at least 2, 3, 4 or 5 times. In certain embodiments, the method of the present invention comprises treatment with at least 6 scheduled cycles.

Patients for Treatment

The therapeutic methods may be further characterized according to the patient to be treated. Preferably, the patient is a human being. In certain embodiments, the patient is an adult human. In certain other embodiments, the patient is at least partially refractory to the first therapeutic agent. In certain other embodiments, the patient is at least partially refractory to the second therapeutic agent. In certain other embodiments, the patient is at least partially refractory to the third therapeutic agent.

IV. TREATMENT EFFICACY AND SAFETY

The therapeutic method of the present invention may be further characterized by the efficacy and safety of the treatment. Preferably, the method provides an acceptable safety profile, with the benefit of treatment outweighing the risk. When tested in a phase II or phase III clinical trial of at least 10 patients with pancreatic cancer, the method of the present invention preferably provides an overall response rate of at least about 10%, a duration of response of at least about 1 month, progression-free survival (PFS) of at least about 1 month, and/or overall survival (OS) of at least about 1 month. Preferably, the phase II or phase III clinical trial comprises at least 15 patients. More preferably, the phase II or phase III clinical trial comprises at least 20 patients. More preferably, the phase II or phase III clinical trial comprises at least 25 patients. More preferably, the phase II or phase III clinical trial comprises at least 50 patients. More preferably, the phase II or phase III clinical trial comprises at least 100 patients. More preferably, the phase II or phase III clinical trial comprises at least 200 patients. More preferably, the phase II or phase III clinical trial comprises at least 300 patients. More preferably, the phase II or phase III clinical trial comprises at least 400 patients. More preferably, the phase II or phase III clinical trial comprises at least 500 patients. Preferably, the method of the present invention provides an overall response rate of at least about 20% in patients. More preferably, the method of the present invention provides an overall response rate of at least about 30%. More preferably, the method of the present invention provides an overall response rate of at least about 40%. More preferably, the method of the present invention provides an overall response rate of at least about 50%. More preferably, the method of the present invention provides an overall response rate of at least about 60%. More preferably, the method of the present invention provides an overall response rate of at least about 70%. More preferably, the method of the present invention provides an overall response rate of at least about 80%. More preferably, the method of the present invention provides an overall response rate of at least about 90%. Preferably, the method of the present invention provides a duration of response, PFS, and/or OS of at least about 2 months. Preferably, the method of the present invention provides a duration of response, PFS, and/or OS of at least about 3 months. Preferably, the method of the present invention provides a duration of response, PFS, and/or OS of at least about 4 months. Preferably, the method of the present invention provides a duration of response, PFS, and/or OS of at least about 5 months. Preferably, the method of the present invention provides a duration of response, PFS, and/or OS of at least about 6 months. Preferably, the method of the present invention provides a duration of response, PFS, and/or OS of at least about 7 months. Preferably, the method of the present invention provides a duration of response, PFS, and/or OS of at least about 8 months. Preferably, the method of the present invention provides a duration of response, PFS, and/or OS of at least about 9 months. Preferably, the method of the present invention provides a duration of response, PFS, and/or OS of at least about 10 months. Preferably, the method of the present invention provides a duration of response, PFS, and/or OS of at least about 11 months. Preferably, the method of the present invention provides a duration of response, PFS, and/or OS of at least about 12 months. Preferably, the method of the present invention provides a duration of response, PFS, and/or OS of at least about 14 months. Preferably, the method of the present invention provides a duration of response, PFS, and/or OS of at least about 16 months. Preferably, the method of the present invention provides a duration of response, PFS, and/or OS of at least about 18 months. Preferably, the method of the present invention provides a duration of response, PFS, and/or OS of at least about 20 months. Preferably, the method of the present invention provides a duration of response, PFS, and/or OS of at least about 24 months. In certain embodiments, the overall response rate, duration of response, and progression-free survival mentioned above are measured in a phase II clinical trial. In certain embodiments, the overall response rate, duration of response, and progression-free survival mentioned above are measured in a phase III clinical trial.

The methods desirably administer a therapeutically effective amount of the indicated compound(s) to the patient. A therapeutically effective amount can be determined based on guidance herein and may, for instance, be an amount of a compound sufficient to inhibit, halt, or cause an improvement in a disorder or condition being treated in a particular subject or subject population. For example, a therapeutically effective amount can be an amount of drug sufficient to slow the progression of a disease, or to prevent or delay its recurrence, such as maintenance treatment to prevent or delay relapse. In a human or other mammal, a therapeutically effective amount can be determined experimentally in a laboratory or clinical setting, or may be the amount required by the guidelines of the United States Food and Drug Administration, or equivalent foreign agency, for the particular disease and subject being treated. It should be appreciated that determination of proper dosage forms, dosage amounts, and routes of administration is within the level of ordinary skill in the pharmaceutical and medical arts.

V. MEDICAL KITS

Another aspect of the invention provides medical kits containing a therapeutic agent and/or pharmaceutical composition described herein, along with instructions for using the kits to treat a disorder described herein. In certain embodiments, the medical kit comprises (i) a first therapeutic agent comprising 6,8-bis(benzylsulfanyl)octanoic acid or a pharmaceutically acceptable salt thereof, and (ii) instructions for treating pancreatic cancer in a patient using the first therapeutic agent in combination with (a) a second therapeutic agent comprising gemcitabine or a pharmaceutically acceptable salt thereof and (b) a third therapeutic agent comprising nab-paclitaxel. The medical kit may be further characterized according to one or more of the features described herein in connection with the Therapeutic Applications herein.

VI. PHARMACEUTICAL COMPOSITIONS

Therapeutic agents described herein may be formulated as a pharmaceutical composition comprising one or more therapeutic agents and a pharmaceutically acceptable carrier. For example, the first therapeutic agent can be formulated as a pharmaceutical composition that, for example, optionally further contains a further anti-cancer agent. A pharmaceutical composition that contains both a first therapeutic agent and a second therapeutic agent may be referred to as a co-formulated composition.

In certain embodiments of the present invention, a therapeutic agent may be formulated as a pharmaceutically-acceptable oil; liposome; oil-water or lipid-oil-water emulsion or nanoemulsion; liquid; or salt, crystalline form, or other solid form delivered in a tablet or capsule. To facilitate such formulations, the therapeutic agent may be combined with a pharmaceutically-acceptable carrier or excipient therefor. Examples of pharmaceutically-acceptable carriers are well known in the art and include those conventionally used in pharmaceutical compositions, such as salts, lipids, buffers, chelating agents, flavorants, colorants, preservatives, absorption promoters to enhance bioavailability, antimicrobial agents, and combinations thereof, optionally in combination with other therapeutic ingredients.

As described in detail below, the pharmaceutical compositions may be specially formulated for administration in solid or liquid form, including those adapted for parenteral administration, for example, by subcutaneous, intramuscular, intravenous or epidural injection as, for example, a sterile solution or suspension, or sustained-release formulation.

Further examples of pharmaceutical formulations of the CPI-613 or pharmaceutically acceptable salt thereof are described in U.S. Pat. No. 8,263,653, the entire disclosure of which is incorporated by reference herein.

Methods of preparing pharmaceutical formulations or pharmaceutical compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

In certain embodiments, one or more of the therapeutic agents are administered by intraparenteral administration. In certain other embodiments, one or more of the therapeutic agents are formulated for inhalational, oral, topical, transdermal, nasal, ocular, pulmonary, rectal, transmucosal, intravenous, intramuscular, subcutaneous, intraperitoneal, intrathoracic, intrapleural, intrauterine, intratumoral, or infusion methodologies or administration, or combinations of any thereof, in the form of aerosols, sprays, powders, gels, lotions, creams, suppositories, ointments, and the like. As indicated above, if such a formulation is desired, other additives known in the art may be included to impart the desired consistency and other properties to the formulation.

In certain embodiments, the pharmaceutical composition comprising the first therapeutic agent is an oral dosage form, such as a dry oral dosage form. In certain embodiments, the pharmaceutical composition comprising the first therapeutic agent is an oral dosage form chosen from tablet, pill, capsule, caplet, powder, granule, solution, suspension, and gel. Oral dosage forms may include pharmaceutically acceptable excipients, such as carriers, diluents, stabilizers, plasticizers, binders, glidants, disintegrants, bulking agents, lubricants, plasticizers, colorants, film formers, flavoring agents, preservatives, dosing vehicles, and any combination of any of the foregoing. Pharmaceutically acceptable excipients are determined in part by the particular composition being administered, as well as by the particular dosing schedule. Accordingly, there is a wide variety of suitable formulations of pharmaceutical compositions of the present invention (see, e.g., *Remington: The Science and Practice of Pharmacy*, 20th ed., Gennaro et al. Eds., Lippincott Williams and Wilkins, 2000).

The oral pharmaceutical composition comprising the first therapeutic agent will generally include at least one inert excipient. Excipients include pharmaceutically compatible binding agents, lubricants, wetting agents, disintegrants, and the like. Tablets, pills, capsules, troches and the like can contain any of the following excipients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring. When the dosage unit form is a capsule, it can contain a liquid excipient such as a fatty oil. In addition, dosage unit forms can contain various other materials that modify the physical form of the dosage unit, for example, coatings of sugar, shellac, or enteric agents. Further, a syrup may contain, in addition to the active compounds, sucrose as a sweetening agent and certain preservatives, dyes, colorings, and flavorings. In certain embodiments, the oral pharmaceutical composition comprising the first therapeutic agent comprises an excipient in an amount of about 5% to about 99%, such as about 10% to about 85%, by weight of the composition, with the first therapeutic agent comprising the remainder. In certain embodiments, pharmaceutically acceptable excipients comprise about 20% to about 80% of the total weight of the composition. In certain embodiments, the pharmaceutical composition comprises the first therapeutic agent in an amount of at least about 40% by weight of the composition, with one or more excipients comprising the remainder. In certain embodiments, the pharmaceutical composition comprises the first therapeutic agent in an amount of at least about 50% by weight of the composition. In certain embodiments, the pharmaceutical composition comprises the first therapeutic agent in an amount of at least about 60% by weight of the composition. In certain embodiments, the pharmaceutical composition comprises the first therapeutic agent in an amount of at least about 70% by weight of the composition. In certain embodiments, the pharmaceutical composition comprises the first therapeutic agent in an amount of at least about 80% by weight of the composition. In certain embodiments, the pharmaceutical composition comprises the first therapeutic agent in an amount of at least about 90% by weight of the composition.

Diluents for solid oral pharmaceutical compositions comprising the first therapeutic agent include, but are not limited to, microcrystalline cellulose (e.g. AVICEL®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit), potassium chloride, powdered cellulose, sodium chloride, sorbitol and talc.

Binders for solid oral pharmaceutical compositions comprising the first therapeutic agent include, but are not limited to, acacia, tragacanth, sucrose, glucose, alginic acid, carbomer (e.g. Carbopol), carboxymethylcellulose sodium, dextrin, ethyl cellulose, gelatin, guar gum, hydrogenated vegetable oil, hydroxyethyl cellulose, hydroxypropyl cellulose (e.g. KLUCEL®), hydroxypropyl methyl cellulose (e.g. METHOCEL®), liquid glucose, magnesium aluminum silicate, maltodextrin, methylcellulose, polymethacrylates, povidone (e.g. KOLLIDON®, PLASDONE®), pregelatinized starch, sodium alginate and starch. In certain embodiments, the pharmaceutical composition comprises a binder in an amount of about 0.5% to about 25%, such as about 0.75% to about 15%, by weight of the composition. In certain embodiments, the pharmaceutical composition comprises a binder in an amount of about 1% to about 10% by weight of the composition.

The dissolution rate of a compacted solid pharmaceutical composition in a patient's stomach may be increased by the addition of a disintegrant to the composition comprising the first therapeutic agent. Disintegrants include, but are not limited to, alginic acid, carboxymethylcellulose calcium, carboxymethylcellulose sodium (e.g. AC-DI-SOL®, PRIMELLOSE®), colloidal silicon dioxide, croscarmellose sodium, crospovidone (e.g. KOLLIDON®, POLYPLASDONE®), guar gum, magnesium aluminum silicate, methyl cellulose, microcrystalline cellulose, powdered cellulose, pregelatinized starch, sodium alginate, sodium starch glycolate (e.g. EXPLOTAB®) and starch. In certain embodiments, the pharmaceutical composition comprises a disintegrant in an amount of about 0.2% to about 30%, such as about 0.2% to about 10%, by weight of the composition. In certain embodiments, the pharmaceutical composition comprises a disintegrant in an amount of about 0.2% to about 5% by weight of the composition.

The oral pharmaceutical composition comprising the first therapeutic agent optionally comprises one or more pharmaceutically acceptable wetting agents. Such wetting agents are preferably selected to maintain the API in close association with water, a condition that is believed to improve bioavailability of the composition. Non-limiting examples of surfactants that can be used as wetting agents include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene, caprylic/capric mono- and diglycerides (e.g., Labrasol™ of Gattefosse), polyoxyethylene castor oil and polyoxyethylene hydrogenated castor oil; polyoxyethylene alkyl ethers, for example polyoxyethylene cetostearyl ether, polyoxyethylene fatty acid esters, for example polyoxyethylene stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefosse), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. In certain embodiments, the pharmaceutical composition comprising the first therapeutic agent comprises a wetting agent in an amount of about 0.25% to about 15%, such as about 0.4% to about 10%, by weight of the composition. In certain embodiments, the pharmaceutical composition comprises a wetting agent in an amount of about 0.5% to about 5% by weight of the composition. In certain embodiments, the pharmaceutical composition comprises a wetting agent that is an anionic surfactant. In certain embodiments, the pharmaceutical composition comprises sodium lauryl sulfate as a wetting agent. In certain embodiments, the pharmaceutical composition comprises sodium lauryl sulfate in an amount of about 0.25% to about 7%, such as about 0.4% to about 4%, by weight of the composition. In certain embodiments, the pharmaceutical composition comprises sodium lauryl sulfate in an amount of about 0.5% to about 2% by weight of the composition.

Lubricants (e.g., anti-adherents or glidants) can be added to improve the flow properties of solid oral compositions comprising the first therapeutic agent and/or to reduce friction between the composition and equipment during compression of tablet formulations. Excipients that may function as lubricants include, but are not limited to, colloidal silicon dioxide, magnesium trisilicate, powdered cellulose, starch, talc and tribasic calcium phosphate. Suitable lubricants further include glyceryl behapate (e.g., Compritol™ 888 of Gattefosse); stearic acid and salts thereof, including magnesium, calcium and sodium stearates; zinc stearate; glyceryl monostearate; glyceryl palmitostearate; hydrogenated castor oil; hydrogenated vegetable oils (e.g., Sterotex™ of Abitec); waxes; boric acid; sodium benzoate; sodium acetate; sodium stearyl fumarate; sodium fumarate; sodium chloride; DL-leucine; PEG (e.g., Carbowax™ 4000 and Carbowax™ 6000 of the Dow Chemical Company); sodium oleate; sodium lauryl sulfate; and magnesium lauryl sulfate. In certain embodiments, an oral pharmaceutical composition comprising the first therapeutic agent comprises a lubricant in an amount of about 0.1% to about 10%, such as about 0.2% to about 8%, by weight of the composition. In certain embodiments, the pharmaceutical composition comprises a lubricant in an amount of about 0.25% to about 5% by weight of the composition. In certain embodiments, the pharmaceutical composition comprises magnesium stearate as a lubricant. In certain embodiments, the pharmaceutical composition comprises colloidal silicon dioxide. In certain embodiments, the pharmaceutical composition comprises talc. In certain embodiments, the composition comprises magnesium stearate or talc in an amount of about 0.5% to about 2% by weight of the composition.

Flavoring agents and flavor enhancers make the oral dosage form comprising the first therapeutic agent more palatable to the patient. Common flavoring agents and flavor enhancers for pharmaceutical products that may be included in the composition of the present invention include maltol, vanillin, ethyl vanillin, menthol, citric acid, fumaric acid ethyl maltol, and tartaric acid.

Compositions may also be colored using any pharmaceutically acceptable colorant to improve their appearance and/or facilitate patient identification of the product and unit dosage level.

Selection of excipients and the amounts to use may be readily determined by formulation scientists based upon experience and consideration of standard procedures and reference works in the field. The solid oral compositions comprising the first therapeutic agent of the present invention include powders, granulates, aggregates and compacted compositions. The dosages may be conveniently presented in unit dosage form and prepared by any of the methods well-known in the pharmaceutical arts. Dosage forms include solid dosage forms like tablets, pills, powders, caplets, granules, capsules, sachets, troches and lozenges. In certain embodiments, the pharmaceutical composition comprising the first therapeutic agent is a tablet. In certain embodiments, the pharmaceutical composition comprising the first therapeutic agent is a spray-dried dispersion. In certain embodiments, the pharmaceutical composition comprising the first therapeutic agent is a spray-dried dispersion comprising at least one polymer chosen from polyacrylate, polymethacrylate, poly(vinylpyrrolidone), hydroxypropyl methyl cellulose (HPMC), cellulose acetate phthalate (CAP), and hydroxypropyl methylcellulose acetate succinate (HPMCAS-M). In certain embodiments, the pharmaceutical composition comprising the first therapeutic agent is a spray-dried dispersion comprising at least one polymer chosen from Eudragit L100, poly(vinylpyrrolidone), hydroxypropyl methyl cellulose (HPMC), cellulose acetate phthalate (CAP), and hydroxypropyl methylcellulose acetate succinate (HPMCAS-M). In certain embodiments, the pharmaceutical composition comprising the first therapeutic agent is a spray-dried dispersion comprising at least one polymer chosen from Eudragit L100, poly(vinylpyrrolidone) viscosity grade K30 (PVP K30), hydroxypropyl methyl cellulose (HPMC), cellulose acetate phthalate (CAP), and hydroxypropyl methylcellulose acetate succinate (HPMCAS-M). In certain embodiments, the pharmaceutical composition comprising the first therapeutic agent is a spray-dried dispersion comprising at least one polymer chosen from Eudragit L100 and hydroxypropyl methylcellulose acetate succinate (HPMCAS-M). In certain embodiments, the pharmaceutical composition comprising the first therapeutic agent is a spray-dried dispersion comprising Eudragit L100. In certain embodiments, the pharmaceutical composition comprising the first therapeutic agent is a spray-dried dispersion comprising hydroxypropyl methylcellulose acetate succinate (HPMCAS-M).

The formulations of the invention may be buffered by the addition of suitable buffering agents.

In certain embodiments, the oral pharmaceutical composition comprising the first therapeutic agent of the present invention is a unit dose composition. In certain embodiments, the pharmaceutical composition contains about 1 mg to about 5000 mg of the first therapeutic agent. In certain embodiments, the pharmaceutical composition contains about 100 mg to about 3000 mg of the first therapeutic agent. In certain embodiments, the pharmaceutical composition contains about 200 mg to about 2000 mg of the first therapeutic agent. In certain embodiments, the pharmaceutical composition contains about 50 mg, 100 mg, 200 mg, 300 mg, 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2500 mg, or 3000 mg of first therapeutic agent. In certain embodiments, the pharmaceutical composition contains about 300 mg, 500 mg, 700 mg, or 1000 mg of the first therapeutic agent.

In certain embodiments, the pharmaceutical composition of the present invention comprises an emulsion, particle, or gel as described in U.S. Pat. No. 7,220,428. In certain embodiments, the pharmaceutical composition is a solid or liquid formulation having from about 0.1% to about 75% w/w lipids or fatty acid components. In certain embodiments, the formulation contains about 0.1% to about 15% w/v lipids and fatty acid components. In certain embodiments, the fatty acid component comprises saturated or unsaturated C4, C5, C6, C7, C8, C9, C10, C11, or C12 fatty acids and/or salts of such fatty acids. Lipids may include cholesterol and analogs thereof.

The description above describes multiple aspects and embodiments of the invention, including therapeutic methods, pharmaceutical compositions, and medical kits. The patent application specifically contemplates all combinations and permutations of the aspects and embodiments.

VII. ILLUSTRATIVE NUMBERED EMBODIMENTS

1. A method for treating pancreatic cancer, comprising administering to a patient in need thereof a therapeutically effective amount of (i) a first therapeutic agent comprising 6,8-bis(benzylsulfanyl)octanoic acid or a pharmaceutically acceptable salt thereof, (ii) a second therapeutic agent comprising gemcitabine or a pharmaceutically acceptable salt thereof, and (iii) a third therapeutic agent comprising nab-paclitaxel, in order to treat the pancreatic cancer.
2. The method of embodiment 1, wherein the pancreatic cancer is metastatic pancreatic cancer.
3. The method of embodiment 1, wherein the pancreatic cancer is locally advanced.
4. The method of any one of embodiments 1-3, wherein the first therapeutic agent is administered no more frequently than once per any seven day period.
5. The method of any one of embodiments 1-3, wherein the first therapeutic agent is administered once per each seven day period for a duration of at least 3 weeks.
6. The method of any one of embodiments 1-5, wherein there is at least seven days between any subsequent administration of the first therapeutic agent to the patient.
7. The method of any one of embodiments 1-3, wherein the first therapeutic agent is administered to the patient on days 1 and 15 of a twenty-eight day cycle.
8. The method of any one of embodiments 1-3, wherein the first therapeutic agent is administered to the patient on days 1, 8, and 15 of a twenty-eight day cycle.
9. The method of any one of embodiments 1-8, wherein the second therapeutic agent is administered to the patient no more frequently than once per any seven day period.
10. The method of any one of embodiments 1-8, wherein the second therapeutic agent is administered to the patient once per each seven day period for a duration of at least 3 weeks.
11. The method of any one of embodiments 1-10, wherein there is at least seven days between any subsequent administration of the second therapeutic agent to the patient.
12. The method of any one of embodiments 1-8, wherein the second therapeutic agent is administered to the patient on days 1 and 15 of a twenty-eight day cycle.
13. The method of any one of embodiments 1-8, wherein the second therapeutic agent is administered to the patient on days 1, 8, and 15 of a twenty-eight day cycle.
14. The method of any one of embodiments 1-13, wherein the third therapeutic agent is administered to the patient no more frequently than once per any seven day period.
15. The method of any one of embodiments 1-13, wherein the third therapeutic agent is administered to the patient once per each seven day period for a duration of at least 3 weeks.
16. The method of any one of embodiments 1-15, wherein there is at least seven days between any subsequent administration of the third therapeutic agent to the patient.
17. The method of any one of embodiments 1-13, wherein the third therapeutic agent is administered to the patient on days 1 and 15 of a twenty-eight day cycle.
18. The method of any one of embodiments 1-13, wherein the third therapeutic agent is administered to the patient on days 1, 8, and 15 of a twenty-eight day cycle.
19. The method of any one of embodiments 1-18, wherein the first therapeutic agent is administered intravenously to the patient.
20. The method of any one of embodiments 1-19, wherein the first therapeutic agent is administered to the patient at a dosage ranging from about 250 mg/m$^2$ to about 1500 mg/m$^2$ on any day the first therapeutic agent is administered to the patient.
21. The method of any one of embodiments 1-19, wherein the first therapeutic agent is administered to the patient at a dosage ranging from about 250 mg/m$^2$ to about 500 mg/m$^2$ on any day the first therapeutic agent is administered to the patient.
22. The method of any one of embodiments 1-19, wherein the first therapeutic agent is administered to the patient at a dosage ranging from about 500 mg/m$^2$ to about 1000 mg/m$^2$ on any day the first therapeutic agent is administered to the patient.
23. The method of any one of embodiments 1-19, wherein the first therapeutic agent is administered to the patient at a dosage ranging from about 1000 mg/m$^2$ to about 1500 mg/m$^2$ on any day the first therapeutic agent is administered to the patient.
24. The method of any one of embodiments 1-19, wherein the first therapeutic agent is administered to the patient at a dosage of about 250 mg/m$^2$ on any day the first therapeutic agent is administered to the patient.
25. The method of any one of embodiments 1-19, wherein the first therapeutic agent is administered to the patient at a dosage of about 500 mg/m$^2$ on any day the first therapeutic agent is administered to the patient.
26. The method of any one of embodiments 1-19, wherein the first therapeutic agent is administered to the patient at a dosage of about 1000 mg/m$^2$ on any day the first therapeutic agent is administered to the patient.
27. The method of any one of embodiments 1-19, wherein the first therapeutic agent is administered to the patient at a dosage of about 1500 mg/m$^2$ on any day the first therapeutic agent is administered to the patient.
28. The method of any one of embodiments 1-27, wherein the second therapeutic agent is administered intravenously to the patient.
29. The method of any one of embodiments 1-28, wherein the second therapeutic agent is administered to the patient at a dosage ranging from about 650 mg/m$^2$ to about 1000 mg/m$^2$ on any day the second therapeutic agent is administered to the patient.
30. The method of any one of embodiments 1-28, wherein the second therapeutic agent is administered to the patient at a dosage ranging from about 650 mg/m$^2$ to about 800 mg/m$^2$ on any day the second therapeutic agent is administered to the patient.
31. The method of any one of embodiments 1-28, wherein the second therapeutic agent is administered to the patient at a dosage ranging from about 800 mg/m² to about 1000 mg/m² on any day the second therapeutic agent is administered to the patient.
32. The method of any one of embodiments 1-28, wherein the second therapeutic agent is administered to the patient at a dosage of about 650 mg/m² on any day the second therapeutic agent is administered to the patient.
33. The method of any one of embodiments 1-28, wherein the second therapeutic agent is administered to the patient at a dosage of about 800 mg/m² on any day the second therapeutic agent is administered to the patient.
34. The method of any one of embodiments 1-28, wherein the second therapeutic agent is administered to the patient at a dosage of about 1000 mg/m² on any day the second therapeutic agent is administered to the patient.
35. The method of any one of embodiments 1-34, wherein the third therapeutic agent is administered intravenously to the patient.
36. The method of any one of embodiments 1-35, wherein the third therapeutic agent is administered to the patient at a dosage ranging from about 80 mg/m² to about 125 mg/m² on any day the third therapeutic agent is administered to the patient.
37. The method of any one of embodiments 1-35, wherein the third therapeutic agent is administered to the patient at a dosage ranging from about 80 mg/m² to about 100 mg/m² on any day the third therapeutic agent is administered to the patient.
38. The method of any one of embodiments 1-35, wherein the third therapeutic agent is administered to the patient at a dosage ranging from about 100 mg/m² to about 125 mg/m² on any day the third therapeutic agent is administered to the patient.
39. The method of any one of embodiments 1-35, wherein the third therapeutic agent is administered to the patient at a dosage of about 80 mg/m² on any day the third therapeutic agent is administered to the patient.
40. The method of any one of embodiments 1-35, wherein the third therapeutic agent is administered to the patient at a dosage of about 100 mg/m² on any day the third therapeutic agent is administered to the patient.
41. The method of any one of embodiments 1-35, wherein the third therapeutic agent is administered to the patient at a dosage of about 125 mg/m² on any day the third therapeutic agent is administered to the patient.
42. The method of any one of embodiments 1-11, wherein the first therapeutic agent and the second therapeutic agent are administered to the patient on the same day.
43. The method of any one of embodiments 1-11 or 42, wherein the first therapeutic agent and the third therapeutic agent are administered to the patient on the same day.
44. The method of any one of embodiments 1-43, wherein the first therapeutic agent is administered to the patient in the form of a pharmaceutical composition comprising 6,8-bis(benzylsulfanyl)octanoic acid and a pharmaceutically acceptable carrier.
45. The method of any one of embodiments 1-43, wherein the first therapeutic agent is administered to the patient in the form of a pharmaceutical composition comprising 6,8-bis(benzylsulfanyl)octanoic acid and an ion pairing agent.
46. The method of any one of embodiments 1-43, wherein the first therapeutic agent is administered to the patient in the form of a pharmaceutical composition comprising 6,8-bis(benzylsulfanyl)octanoic acid and triethanolamine.
47. The method of any one of embodiments 1-43, wherein the first therapeutic agent is 6,8-bis(benzylsulfanyl)octanoic acid in the form of an ion pair with triethanolamine.
48. The method of any one of embodiments 1-47, wherein the second therapeutic agent is gemcitabine hydrochloride.
49. The method of any one of embodiments 1-48, wherein the third therapeutic agent is nab-paclitaxel.
50. The method of any one of embodiments 1-49, wherein the patient is an adult human.
51. The method of any one of embodiments 1-50, wherein the patient is at least partially refractory to the first therapeutic agent.
52. The method of any one of embodiments 1-51, wherein the patient is at least partially refractory to the second therapeutic agent.
53. The method of any one of embodiments 1-52, wherein the patient is at least partially refractory to the third therapeutic agent.
54. A medical kit, comprising (i) a first therapeutic agent comprising 6,8-bis(benzylsulfanyl)octanoic acid or a pharmaceutically acceptable salt thereof, and (ii) instructions for treating pancreatic cancer in a patient using the first therapeutic agent in combination with (a) a second therapeutic agent comprising gemcitabine or a pharmaceutically acceptable salt thereof and (b) a third therapeutic agent comprising nab-paclitaxel.

VIII. EXAMPLES

The invention now being generally described, will be more readily understood by reference to the following examples, which are included merely for purposes of illustration of certain aspects and embodiments of the present invention, and are not intended to limit the invention.

Example 1—Treatment of Pancreatic Cancer in Human Patients Using a Combination of 6,8-Bis(benzylsulfanyl)octanoic Acid Triethanolamine Ion Pair in Combination with Gemcitabine Hydrochloride and Nab-Paclitaxel Human patients suffering from locally advanced or metastatic pancreatic cancer are to be administered 6,8-bis(benzylsulfanyl)octanoic acid triethanolamine ion pair in combination with gemcitabine hydrochloride and nab-paclitaxel. Experimental procedures are described below.
Study Design
This is a single arm, open-label study, and investigators and subjects are not blinded to the treatment.
Treatment Schedule and Follow Up
Subjects will be followed for survival until death, loss to follow-up, or study completion. Study completion is 1 year after the last subject starts study drug treatment. At least six months of treatment is recommended for patients who have a response, unless or until:
  Patients exhibited disease progression in the opinion of the principal investigator
  Unacceptable treatment toxicity
  Patient withdrawal of consent
  Investigator's discretion to withdraw patients from the study because continued participation in the study is not in the patient's best interest.
  Undercurrent illness: a condition, injury, or disease unrelated to the intended disease for which the study is investigating, that renders continuing the treatment unsafe or regular follow-up impossible General or specific changes in the patient's condition that renders the patient ineligible for further investigational treatment Non-compliance with investigational treatment, protocol-required evaluations or follow-up visits Termination of the clinical trial by the sponsor.

When terminating treatment during this trial, the investigator should make every effort to contact the patient and to perform a final evaluation. Also, the reason(s) for withdrawal from the study must be recorded. Survival and post-study treatment will be documented bi-monthly after patient completes participation on this trial.

Screening

At least two patients per month are expected to be screened.

Patient Inclusion Criteria

1. Histologically or cytologically documented and measurable locally advanced and metastatic pancreatic adenocarcinoma.
2. Eastern Cooperative Oncology Group (ECOG) performance status 0-2.
3. First line treatment for patients diagnosed with metastatic disease.
4. First line treatment for patients with locally advanced pancreatic cancer who have not been treated with systemic therapies or local treatment with chemoradiation.
5. Expected survival >3 months.
6. Women of child-bearing potential must use accepted contraceptive methods (abstinence, intrauterine device, oral contraceptive, or double barrier device) during the study, and must have a negative serum or urine pregnancy test within 1 week prior to treatment initiation.
7. Fertile men must practice effective contraceptive methods during the study, unless documentation of infertility exists.
8. Laboratory values ≤2 weeks must be:
   A. Adequate hematologic (platelet count ≥100,000 cells/mm$^3$ or ≥100 bil/L; absolute neutrophil count [ANC]≥1500 cells/mm3 or ≥1.5 bil/L; and hemoglobin ≥9 g/dL or ≥90 g/L).
   B. Adequate hepatic function (aspartate aminotransferase [AST/SGOT]≤3× upper normal limit [UNL], alanine aminotransferase [ALT/SGPT]≤3× UNL (≤5× UNL if liver metastases present), Total bilirubin ≤1.5× UNL.
   C. Adequate renal function (serum creatinine ≤2.0 mg/dL or 177 μmol/L).
   D. Adequate coagulation (International Normalized Ratio or INR must be ≤1.5), unless the patient receives anticoagulation treatment in which case the INR should be within the therapeutic level, not higher than 3.5.
   E. Albumin >2.5 g/dL.
9. No evidence of clinically significant active infection.
10. Mentally competent, ability to understand and willingness to sign the informed consent form.

Patient Exclusion Criteria
1. Unwilling or unable to follow protocol requirements. Endocrine or acinar pancreatic carcinoma.
2. Known cerebral metastases, central nervous system (CNS), or epidural tumor.
3. Prior treatment with any systemic chemotherapy for metastatic adenocarcinoma of the pancreas or for stage III (locally advanced) adenocarcinoma.
4. Presence of clinically significant abdominal ascites.
5. Patients receiving any other standard or investigational treatment for their cancer, or any other investigational agent for any indication within the past 2 weeks prior to initiation of CPI-613 treatment.
6. Serious medical illness that would potentially increase patients' risk for toxicity.
7. Any active uncontrolled bleeding, and any patients with a bleeding diathesis (e.g., active peptic ulcer disease).
8. Pregnant women, or women of child-bearing potential not using reliable means of contraception (because the teratogenic potential of CPI-613 is unknown).
9. Lactating females.
10. Fertile men unwilling to practice contraceptive methods during the study period.
11. Life expectancy less than 3 months.
12. Any condition or abnormality which may, in the opinion of the investigator, compromise the safety of patients.
13. Unwilling or unable to follow protocol requirements.
14. Active heart disease including but not limited to symptomatic congestive heart failure (NYHA class 3 or 4), symptomatic coronary artery disease, symptomatic angina pectoris, or symptomatic myocardial infarction.
15. Patients with a history of myocardial infarction that is <3 months prior to registration.
16. Evidence of clinically significant active infection.
17. Patients with known HIV infection.
18. Patients who have received cancer immunotherapy of any type within the past 2 weeks prior to initiation of CPI-613 Compound treatment. Steroid use for contrast induced allergy or other supportive care indication is allowed.
19. Requirement for immediate palliative treatment of any kind including surgery.
20. Any other malignancy within last 3 years.
21. History of interstitial lung disease, idiopathic pulmonary fibrosis or pulmonary hypersensitivity pneumonitis.
22. Peripheral neuropathy grades 2 or higher.

Study Procedures

CPI-613 Drug Compound will be administered on day 1, day 8, and day 15 in combination with gemcitabine hydrochloride and nab-paclitaxel given on day 1, day 8, and day 15, on a 28-day cycle. CPI-613 Drug Compound is 6,8-bis (benzylsulfanyl)octanoic acid triethanolamine ion pair.

Key study procedures are summarized in the following Table.

| Treatment Cycle | | Administration of CPI-613 Drug Compound |
|---|---|---|
| Cycle | Day | and Nappaclitaxel + gemcitabine |
| Each Cycle | Day 1, 8, 15 | CPI-613 Drug Compound: IV infusion at a rate of 4 mL/min via a central venous catheter at 500 mg/m$^2$ (with concurrent D5W infusing at a rate of 125-150 cc/hr). At any dose above 500 mg/m$^2$ the infusion will be over 2 hours. The dose of CPI-613 Drug Compound will be determined based on cohort as described below. Nab-paclitaxel 125 mg/m$^2$ intravenous administration over 30 minutes, followed by 1000 mg/m$^2$ gemcitabine hydrochloride intravenous administration over 30 minutes. |

The primary endpoints of this pilot study are to establish the MTD, describe the safety profile, and determine the clinical activity as measured by RR of CPI-613 Drug Compound in combination with gemcitabine hydrochloride and nab-paclitaxel.

The definition of a dose-limiting toxicity (DLT) evaluation period will consist of 1 cycles (4 weeks).

A modified 3+3 design will be implemented during the dose escalation part of the study. Initially, 3 patients will be enrolled at Dose Level 1:

If 2 of 3 patients experience a dose-limiting toxicity (DLT) within the DLT evaluation period, then dose escalation will stop, and Dose Level 1 will be considered above the MTD and 3 patients will be treated at Dose Level −1. If more than 1 patient experiences a DLT at dose level −1 then 3 patients will be treated at Dose Level −2. If more than 1 patient experiences a DLT at dose level −2 the study will revert back to the original schedule of treatment on day 1 and day 15 and 3 more patients will be enrolled on dose level 1 and dose escalation will continue using the d1, d15 schedule only.

If 0 of 3 patients experience a DLT within the DLT evaluation period, the dose will be escalated to Dose Level 2 in the next cohort.

If 1 of 3 patients experiences a DLT within the DLT evaluation period, then an additional 3 patients will be enrolled at Dose Level 1.

If at most 1 of 6 patients experience a DLT during the DLT evaluation period, then the dose will be escalated to Dose Level 2 in the next cohort.

If more than 1 of 6 patients experience a DLT during the DLT evaluation period, then dose escalation will stop, and Dose Level 1 will be considered above the MTD and 3 patients will be treated at Dose Level −1. If more than 1 patient experiences a DLT at dose level −1 then 3 patients will be treated at Dose Level −2. If more than 1 patient experiences a DLT at dose level −2 the study will revert back to the original schedule of treatment on day 1 and day 15 and 3 more patients will be enrolled on dose level 1 and dose escalation will continue using the d1, d15 schedule only.

If escalation proceeds to Dose Level 2, 3 patients will be initially enrolled at Dose Level 2:

If 2 of 3 patients experience a DLT during the DLT evaluation period, then Dose Level 1 will be considered the MTD.

If 0 of 3 patients experience a DLT during the DLT evaluation period, then the dose will be escalated to Dose Level 3 in the next cohort.

If 1 of 3 patients experience a DLT during the DLT evaluation period, an additional 3 patients will be enrolled at Dose Level 2.

If at most 1 of 6 patients experience a DLT during the DLT evaluation period, then the dose will be escalated to Dose Level 3 in the next cohort.

If more than 1 of 6 patients experience a DLT during the DLT evaluation period, then Dose Level 1 will be considered the MTD.

If escalation proceeds to Dose Level 3, 3 patients will be initially enrolled at Dose Level 3:

If 2 of 3 patients experience a DLT during the DLT evaluation period, then Dose Level 2 will be considered the MTD.

If 0 of 3 patients experience a DLT during the DLT evaluation period, then dose escalation will stop, and Dose Level 3 will be considered the MTD. No doses higher than Dose Level 3 will be evaluated.

If 1 of 3 patients experience a DLT during the DLT evaluation period, an additional 3 patients will be enrolled at Dose Level 3.

If at most 1 of 6 patients experience a DLT during the DLT evaluation period, then dose escalation will stop and Dose Level 3 will be considered the MTD. No doses higher than Dose Level 3 will be evaluated.

If more than 1 of 6 patients experience a DLT during the DLT evaluation period, then Dose Level 2 will be considered the MTD.

An additional cohort of 6 patients will be enrolled at the MTD for further toxicity assessment and assessment of preliminary clinical activity.

Patients enrolled at the MTD will be included in a preliminary assessment of clinical activity of the combination, as measured by RR. If the preliminary assessment of clinical activity (as assessed by the principal investigator) demonstrates a response rate of 40% or greater, the current study may be amended to include an expanded cohort of patients treated in an open-label Phase II portion.

Based on the excellent tolerance of a modified chemotherapy regimen in combination with CPI-613 Drug Compound at 500 mg/m$^2$ (with respect to) and Gemcitabine+nab-paclitaxel on days 1 and 15 the trial has been amended to explore the tolerability of the standard of care approved regimen with Gemcitabine+nab-paclitaxel given on days 1, 8, and 15.

The following dose level escalation is proposed bellow. CPI 613 will be administered only if chemotherapy is administered based on standard parameters for chemotherapy.

The dose modifications for hematologic toxicity induced by chemotherapy are described herein.

| Dose Level | Gemcitabine Hydrochloride (mg/m$^2$ d1, d8, and d15) | nab-paclitaxel (mg/m$^2$ IV d1, d8, and d15) | CPI-613 Drug Compound (mg/m$^2$ IV d1, d8, and d15 with respect to 6,8-bis(benzylsulfanyl)octanoic acid) |
|---|---|---|---|
| −2 | 650 | 80 | 250 |
| −1 | 800 | 100 | 250 |
| 1 | 1000 | 125 | 500 |
| 2 | 1000 | 125 | 1000 |
| 3 | 1000 | 125 | 1500 |

If dose level "−2" is not tolerated (>1 patient with a DLT) with the new chemotherapy backbone of gemcitabine hydrochloride+nab-paclitaxel days 1, 8, and 15 then the day 8 will be dropped, as proposed below.

| Dose Level | Gemcitabine Hydrochloride (mg/m$^2$ d1, and d15) | nab-paclitaxel (mg/m$^2$ IV d1, d15) | CPI-613 Drug Compound (mg/m$^2$ IV d1, d15 with respect to 6,8-bis(benzylsulfanyl)octanoic acid) |
|---|---|---|---|
| −2 | 650 | 80 | 250 |
| −1 | 800 | 100 | 250 |
| 1 | 1000 | 125 | 500 |
| 2 | 1000 | 125 | 1000 |
| 3 | 1000 | 125 | 1500 |

Toxicity and Safety Assessments: Toxicity will be assessed at every visit using National Cancer Institute-Common Terminology Criteria for Adverse Events (NCI-CTCAE) version 4.0. Safety assessments will be performed on the day of each treatment. Safety assessments will include vital signs, ECOG performance status, medical history, physical examination, review of concomitant medications, complete blood count (CBC), chemistries with liver function tests, and CA 19-9. Symptom management and supportive care will be provided as clinically indicated to ensure optimal patient care. After discontinuation of study treatment, subjects will have safety assessments 30 days after the last dose of study drug.

Clinical chemistry to be assessed includes:

| | |
|---|---|
| glucose | BUN |
| creatinine | AST/serum glutamic-oxaloacetic transaminase (SGOT) |
| total protein | ALT/serum glutamic-pyruvic transaminase (SGPT) |
| albumin | alkaline phosphatase (ALP) |
| Na+ | total bilirubin |
| K+ | |
| Cl− | |
| Mg | |
| Ca+2 | |
| PO4 | |
| CO2 | |

Hematology includes:

| | |
|---|---|
| complete blood count | hemoglobin |
| differential count | hematocrit |
| platelet count | |

Coagulation includes:

| | |
|---|---|
| Prothrombin time | Partial thromboplastin time |

Efficacy: Efficacy will be assessed by Response Evaluation Criteria in Solid Tumors Version 1.1 (RECIST 1.1) criteria using pancreatic protocol CT scan with iv contrast of the chest, abdomen, and pelvis every 2 cycles and as clinically indicated. Patients who are determined by the principal investigator to have progressed will be removed from the study, while those who are determined to have stable disease or favorable response will continue, with subsequent re-imaging after each 2 cycles until unacceptable toxicity or progression.

OS will be monitored bimonthly via telephone contact after treatment termination. OS and PFS will be calculated from the first day of treatment. The duration of OS will be measured until the date of death or censored at follow-up. The duration of response (evaluated by PFS) will be measured from the date a first objective response is documented until the first sign of progression assessed by MRI. RR is defined as % of patients who experienced a Complete Response (CR) or Partial Response (PR). CR and PR are based on Response Evaluation Criteria in Solid Tumor (RECIST) Version 1.1. The best response recorded from the start of the treatment until Disease Progression (DP) will be considered.

Correlatives: Sample collection for this study will include the following:
1. Plasma and serum at baseline, day 1 of every 28-day cycle, and at disease progression.
2. PK samples drawn Cycle 1 Day 1 pre-dose, 15′, 30′, 60′, 90′, 120′, 150′, 180′, and 240′ from the start of the infusion and Cycle 2 Day 1 pre-dose for 3 patients treated at each different dose level.
3. Urine sample (10-15 ml) of the first void on Cycle 1 Day 1 following the CPI-613 infusion if the patient can provide a sample.

Dosing Delay and Dose Modification
Dosage Adjustment for CPI-613 Drug Compound-Related Toxicities For adverse events unrelated to serum creatinine elevation or reduction in renal function but are possibly related to CPI-613 Drug Compound, the occurrence of Grade 1 toxicity does not generally require dose modification for subsequent doses for that patient. However, if Grade 2 toxicity (other than alopecia and nausea) probably related to CPI-613 Drug Compound develops, treatment is to be withheld and can resume only after the Grade 2 toxicity has been reduced to Grade 1 or below, and the dose level for subsequent doses for that patient will be reduced by 25% of the dose at which such Grade 2 toxicity occurs. Grade 2 alopecia and nausea do not require withholding treatment or dose reduction. If Grade 3 or 4 toxicity probably related to CPI-613 Drug Compound develops, dosing of CPI-613 Drug Compound of that patient will be withheld and the patient shall be monitored for recovery from, and reversibility of, such Grade 3 or 4 toxicity. To resume treatment with CPI-613 Drug Compound for a patient who has had CPI-613-Drug Compound-related Grade 3 or 4 toxicity, the Grade 3 or 4 toxicity must be reduced to Grade 1 or below, and the dose level for subsequent doses for that patient will be reduced to 50% of the dose at which such Grade 3 or 4 toxicity occurs.

For adverse events related to creatinine elevation or reduction in renal function that are possibly related to CPI-613 Drug Compound, dosing of the patient will be withheld even if the severity level is Grade 2 or above. Treatment can resume only after the toxicity has been reduced to Grade 1. The dose level for subsequent doses for that patient will be reduced by 15% if the severity level is of Grade 1, by 25% for Grade 2 toxicity, and by 50% for Grade 3 or 4 toxicity.

The CPI-613 Drug Compound is not expected to contribute to hematologic toxicity and therefore the hematologic toxicity will be attributed to the chemotherapy agents (gemcitabine and nab-Paclitaxel) and the dose modifications are described below.

Dosage Adjustment for Gemcitabine Hydrochloride and/or Nab Paclitaxel Hematologic-Related Toxicities

| DRUG | INITIAL DOSE | DOSE REDUCTION LEVEL 1 | DOSE REDUCTION LEVEL 2 |
|---|---|---|---|
| Gemcitabine Hydrochloride | 1000 mg/m$^2$ | 800 mg/m$^2$ | 650 mg/m$^2$ |
| NAB-Paclitaxel | 125 mg/m$^2$ | 100 mg/m$^2$ | 80 mg/m$^2$ |

Neutropenia:
For grade 2 or higher neutropenia, hold treatment for up to 2 weeks until recovery to at least grade 1. If patient has not recovered to grade 1 or less in 2 weeks, discontinue treatment. Follow drug specific modifications below for subsequent cycles. It is recommended that Pegfilgrastim, 6 mg subcutaneously be administered with each subsequent day 15 dose of gemcitabine hydrochloride/nab-paclitaxel.

| Toxicity grade | Modification Gemcitabine Hydrochloride | Modification Nab-Paclitaxel |
|---|---|---|
| 2 | maintain dose | maintain dose |
| 3-4 | 1$^{st}$ occurrence reduce dose by 1 level 2$^{nd}$ occurrence reduce dose by 1 level 3$^{rd}$ occurrence discontinue | 1$^{st}$ occurrence reduce dose by 1 level 2$^{nd}$ occurrence reduce dose by 1 level 3$^{rd}$ current discontinue |

Thrombocytopenia:
For grade 2 or higher thrombocytopenia, hold treatment for up to 2 weeks until recovery to at least grade 1. If patient has not recovered to grade 1 or less in 2 weeks discontinue treatment. Follow drug specific modification below for subsequent cycles.

| Toxicity grade | Modification Gemcitabine Hydrochloride | Modification Nab-Paclitaxel |
| --- | --- | --- |
| 2 | maintain dose | maintain dose |
| 3-4 | 1$^{st}$ occurrence reduce dose by 1 level | 1$^{st}$ occurrence reduce dose by 1 level |
| | 2$^{nd}$ occurrence reduce dose by 1 level | 2$^{nd}$ occurrence reduce dose by 1 level |
| | 3$^{rd}$ occurrence discontinue | 3$^{rd}$ current discontinue |

Peripheral sensory neuropathy-dose modifications for nab-Paclitaxel only:

| Toxicity grade | duration of toxicity 1-7 day | >7 days | persistent between cycle |
| --- | --- | --- | --- |
| 2 | no dose modification | no dose modification | next lowest dose level for nab-paclitaxel |
| 3 | next lowest dose level for nab-paclitaxel | next close dose level for Nab paclitaxel | discontinue |
| 4 | discontinue | discontinue | discontinue |

Permanently discontinue gemcitabine hydrochloride for any of the following:
  Unexplained dyspnea or other evidence of severe pulmonary toxicity.
  Severe hepatic toxicity.
  Hemolytic-Uremic Syndrome.
  Capillary Leak Syndrome.
  Posterior reversible encephalopathy syndrome.
  Withhold gemcitabine hydrochloride or reduce dose by 50% for other severe (Grade 3 or 4) non-hematological toxicity until resolved. No dose modifications are recommended for alopecia, nausea, or vomiting.

Dosage Adjustment for nab-Paclitaxel-Related Toxicities
  Liver Function:
    a. AST less than 10 times the upper limit of normal (ULN) and total bilirubin 1.26 to 2 times ULN, reduce dose by 25%.
    b. AST less than 10 times ULN and total bilirubin 2.01 to 5 times ULN, reduce dose by
    c. AST greater than or equal to 10 times ULN and/or total bilirubin greater than 5 times ULN, use is not recommended.

Duration of Treatment for Each Patient at Each Cohort
At least six months of treatment is recommended for patients who have a response, unless or until:
  Patients exhibited disease progression in the opinion of the principal investigator.
  Unacceptable treatment toxicity.
  Patient withdrawal of consent.
  Investigator's discretion to withdraw patients from the study because continued participation in the study is not in the patient's best interest.
  Undercurrent illness: a condition, injury, or disease unrelated to the intended disease for which the study is investigating, that renders continuing the treatment unsafe or regular follow-up impossible.
  General or specific changes in the patient's condition that renders the patient ineligible for further investigational treatment.
  Non-compliance with investigational treatment, protocol-required evaluations or follow-up visits.
  Termination of the clinical trial by the sponsor.

Responding patients with acceptable tolerance to therapy (with dose modifications per protocol as needed) should continue on therapy unless or until a criterion for removal from study occurs as listed above.

When terminating treatment during this trial, the investigator should make every effort to contact the patient and to perform a final evaluation. Also, the reason(s) for withdrawal from the study must be recorded.

Survival and post-study treatment will be documented bi-monthly after patient completes participation on this trial. All patients will be followed until death.

Statistical Plans

The Safety analysis set (SAF) consists of all subjects enrolled on the study who receive at least one dose of any study treatment.

A 3+3 design will be used to assess the MTD during the dose escalation part of the study.

Disposition, Demographics and Baseline Characteristics

The number and percentage of patients enrolled in each dose level will be tabulated. Demographic information and other Baseline Characteristics (e.g. disease characteristics, medical history, ECOG performance status) will be summarized by dose level.

Concomitant Medications

The number and percentage of subjects with concomitant medications will be described by dose level in a summary table and a listing provided.

Safety Assessment

Patients in the Safety Analysis Set will be included in the safety analysis. Exposure to study drug will be summarized (e.g. number of cycles CPI-316, duration of exposure) descriptively.

Definition of Serious Adverse Events

An AE or suspected adverse reaction is considered "serious" if, in the view of either the investigator or sponsor, it results in any of the following outcomes: death, a life-threatening adverse event, inpatient hospitalization or prolongation of existing hospitalization, a persistent or significant incapacity or substantial disruption of the ability to conduct normal life functions, or a congenital anomaly/birth defect. Important medical events that may not result in death, be life-threatening, or require hospitalization may be considered serious when, based upon appropriate medical judgment, they may jeopardize the patient or subject and may require medical or surgical intervention to prevent one of the outcomes listed in this definition. Examples of such medical events include allergic bronchospasm requiring intensive treatment in an emergency room or at home, blood dyscrasias or convulsions that do not result in inpatient hospitalization, or the development of drug dependency or drug abuse.

Severity of event
  1. Mild: Events require minimal or no treatment and do not interfere with the participant's daily activities.
  2. Moderate: Events result in a low level of inconvenience or concern with the therapeutic measures. Moderate events may cause some interference with functioning.
  3. Severe: Events interrupt a participant's usual daily activity and may require systemic drug therapy or other treatment. Severe events are usually potentially life-threatening or incapacitating.

Hematology, biochemistry, and CA 19-9 laboratory values and ECOG performance status will be summarized descriptively by dose level. Patients who have laboratory values outside the range of normal will have their laboratory values presented in a listing.

Preliminary Efficacy Assessment

As patients are required to have measurable disease per inclusion criteria, the Safety analysis set will be used to assess preliminary efficacy. Patients who do not have an evaluable baseline or follow-up scan will have a Best Overall Response (per RECIST v1.1) designation of NE (Not Evaluable) and will be included in the denominator of the response rate calculation.

Efficacy will be assessed in a preliminary manner during the dose escalation phase of the study with the following endpoints:

Tumor Response Rate (RR): Defined as the proportion of patients with complete or partial response (CR or PR) per RECIST v1.1.

Progression-Free Survival (PFS): A PFS event is defined as the date of death or of the first scan showing disease progression by investigator assessment, whichever occurs first. PFS is defined in months as (date of PFS event–date of first dose of study treatment+1)/30.4375. Patients who are not observed to have a PFS event are censored at the date of last disease assessment.

Overall Survival (OS): OS is defined in months as (date of death–date of first dose of study treatment+1)/30.4375. Patients who are not known to have died will be censored at the date last known alive.

Tumor response rate will be summarized by dose level, and an exact 95% confidence interval (using the Copper-Pearson method) will be calculated for the response rate.

Median PFS and OS will be described in a summary table, and supportive Kaplan-Meier plots will be created to describe these endpoints.

Sample Size and Power

Dose Escalation

The 3+3 design will be implemented for the dose escalation. A planned maximum of 18 patients (6 at each dose level) will be enrolled during the dose escalation. Once the MTD is determined, an additional 6 patients will be enrolled at the MTD for further assessment of toxicity and preliminary clinical activity. Thus, the dose escalation part of the study will enroll a total planned maximum of 24 patients. Enrollment may be higher or lower depending on the toxicity observed or need to replace patients who do not complete the DLT evaluation period for reasons other than a DLT.

The study may continue on to an open-label Phase II part if the observed preliminary tumor response rate (per investigator assessment) in patients enrolled at the MTD is at least 40%. The design plans for up to 12 patients to be enrolled at the MTD. With 12 patients, 5 responses would be required to reach the 40% threshold. A 95% exact CI for this proportion of 0.417 would be (0.152, 0.723).

With 12 patients, an adverse event with an overall frequency of 1% will be observed with a probability of 11.4%. For an adverse event with an overall frequency of 5%, the probability of observing at least one such event is 46%.

Open-Label Phase II

If the study proceeds to the open-label Phase II portion, a Simon's two-stage design will be implemented to establish preliminary efficacy for further study. The null hypothesis that the true confirmed tumor response rate is 23% will be tested against a one-sided alternative of 40%. In the first stage, 24 patients will be accrued at the MTD. If there are 5 or fewer confirmed responses, the study will stop. Otherwise, 22 additional patients will be enrolled for a total of 46 patients. If, in 46 patients, 16 or more responses are observed, the null hypothesis will be rejected. This design has 80% power to reject the null hypothesis when an alternative hypothesis of 40% and one-sided alpha=0.05.

Thus, if both parts of the study are completed, the total planned maximum sample size for the entire study is 70 patients.

Available Resources

1. PI anticipates no issue with recruitment as they will be part of the standard patients that she sees in her private practice.
2. Subjects will be seen during regular clinic hours. Additionally, study coordinator and PI will meet regularly. There will be bi weekly meetings to discuss patient care.
3. Study coordinators are RN's who are trained according to AHS research requirements. Additionally, we have data and regulatory compliance associates who perform data management requirements as well as regulatory submission requirements to the IRB and sponsor.
4. Participating investigators' offices and the Oncology Research office at MMC and Overlook will be used for consenting patients. Patients will be seen at the investigators offices for study related physician visits.
5. PI and Sub-I's are MD's who can provide appropriate medical assessment and determination. The oncology service line offers social work support as needed.
6. The sponsor will provide training at the Site Initiation visit. Investigator and study coordinator will provide additional training as needed to participants who are unable to attend the SIV.

Reportable Events

Adverse Event Characteristics

CTCAE term (AE description) and grade: The CTEP Active Version of the NCI Common Terminology Criteria for Adverse Events (CTCAE 4.0) will be utilized for AE reporting.

All appropriate treatment areas should have access to a copy of the CTEP Active Version of CTCAE.

'Expectedness': AEs can be 'Unexpected' or 'Expected' for expedited reporting purposes only.

Attribution of the AE:
Definite—The AE is clearly related to CPI-613 Drug Compound.
Probable—The AE is likely related to CPI-613 Drug Compound.
Possible—The AE may be related to CPI-613 Drug Compound.
Unlikely—The AE is doubtfully related to CPI-613 Drug Compound.
Unrelated—The AE is clearly NOT related to CPI-613 Drug Compound.

The Red Cap Database will be used for this study to monitor dose level accrual and toxicity-related data. All grade 3, 4, 5 adverse events are to be reported.

List of Adverse Events for CPI-613 Drug Compound

Possibly Related:
Alkaline phosphatase
Anorexia
ALT (SGPT)
AST (SGOT)
Bilirubin (hyperbilirubinemia)
Calcium (hypercalcemia, hypocalcemia)
Flushing
Hemoglobin (anemia)
*Injection site Reaction
Leukocytes
Lymphopenia
Neutrophils (neutropenia)

Platelets (thrombocytopenia)
Potassium
Sodium
Probably Related:
*Creatinine
*Vomiting
*Nausea
*Diarrhea
Asterisk (*) denotes expected Adverse Events.
List of Adverse Events for Gemcitabine
*Neutropenia—definitely related
*Thrombocytopenia—definitely related
*Anemia—definitely related
*Interstitial pneumonitis—definitely related
*Pulmonary fibrosis—definitely related
Pulmonary edema—possibly related
*Adult Respiratory Distress Syndrome—possibly related
*Hemolytic—uremic syndrome—definitely related
Liver injury—possibly related
*Capillary leak syndrome—definitely related
*Posterior reversible encephalopathy syndrome—definitely related
Asterisk (*) denotes expected Adverse Events.
List of Adverse Events for Nab-Paclitaxel
*Nausea—definitely related
*vomiting—definitely related
*Indigestion—probably
*Diarrhea—probable
Mouth sores—probably
Headache—possibly
Muscle or joint pain—possibly
*Numbness/tingling/burning of the hands or feet—definitely
Weakness—possibly
Dizziness—possibly
Dehydration—possible
Hypokalemia—possible
*Anemia—definitely
*temporary hair loss—definitely
*Easy bruising or bleeding, skin rash—possibly
fast/slow/irregular heartbeat—probable
pain/redness/swelling/weakness of the arms or legs
calf pain or swelling that is warm to the touch—possibly
vision changes—probable
Infection: (primarily included oral candidiasis, respiratory tract infection, and pneumonia)—possibly Definition of DLT and DLT Evaluation Period A dose limiting toxicity is defined as the occurrence of any clinically relevant Grade ≥3 toxicity at least possibly related to the CPI-613 Drug Compound. The following toxicities from any source are excluded from defining a DLT: Grade 3 nausea and vomiting responsive to anti-emetics unless they are >7 consecutive days in spite of anti-emetic treatment; Grade 3 diarrhea responsive to anti-diarrheal therapy unless it is >7 consecutive days in spite of antidiarrheal therapy; Grade 3 or 4 neutropenia lasting <7 days; Grade 3 thrombocytopenia; Grade 3 or 4 metabolic derangements attributed to tumor lysis syndrome unless metabolic derangement is >7 days; or antimicrobial medications that correct with oral or IV supplementation.

The DLT evaluation period is through Cycle 1 (4 weeks) for each patient.

Reconstitution and Administration of CPI-613 Drug Compound

CPI-613 Drug Compound must be diluted from 50 mg/mL to 12.5 mg/mL with 5% Dextrose Water or D5W (i.e., 1 portion of CPI-613 Drug Compound diluted with 3 portions of D5W) prior to administration. The diluted drug product should be visually inspected for clarity. If haziness, precipitate or coloration (other than colorless) is observed, do not use the diluted drug product for dosing. After dilution with sterile D5W, the solution is clear and has a pH of 8.4-8.8. The diluted CPI-613 drug product has been found to be stable for 24 hrs at room temperature and refrigeration temperature.

CPI-613 Drug Compound must be administered IV, via an IV catheter that is free flowing and free of air in the dead space of the IV catheter, to minimize vascular irritation, inflammation and acute toxicity of CPI-613 Drug Compound. To avoid local reactions at and around the site of administration, CPI-613 Drug Compound must be administered via a central venous catheter.

CPI-613 Drug Compound must not be administered as a bolus, but by infusion, at a rate of ~4 mL/min, via a central venous catheter with D5W running at a rate of about 125-150 mL/hr for a dose of 500 mg/m$^2$. At any dose above 500 mg/m$^2$ the infusion will be over 2 hours. This is to minimize potential acute toxicity of CPI-613 Drug Compound.

The following precautions must be taken when administering CPI-613 Drug Compound:
A. Confirmation of the placement of the IV line to ensure a lack of leakage of CPI-613 Drug Compound into the perivascular space.
B. Confirmation that the IV line is free flowing.
C. Confirmation that the IV line is free of dead air space.
D. Dilute CPI-613 Drug Compound with D5W, as instructed in the study protocol.
E. Administer CPI-613 Drug Compound by infusion, not as a bolus.
F. After administration of CPI-613 Drug Compound, flush the IV line with ~10 mL of D5W to remove residual CPI-613 Drug Compound.
G. To avoid local reactions at and around the site of administration, CPI-613 Drug Compound should be administered via a central venous catheter.

Example 2—Oral Efficacy of 6,8-Bis(benzylsulfanyl)octanoic Acid in Non-Small Cell Lung Cancer Human H460 NSCLC cells were obtained from American Type Cell Culture (ATCC) (catalog no. HTB-177, Manassas, Va.). These cells tested negative for viral contamination using the Mouse Antibody Production (MAP) test, performed by Charles River Labs Molecular Division, upon the receipt of the tumor cells from ATCC. The tumor cells were maintained at 3TC in a humidified 5% CO2 atmosphere in T225 tissue culture flasks containing 50 mL of Roswell Park Memorial Institute (RPMI)-1640 solution with 10% Fetal Bovine Serum (FBS) and 2 mM L-glutamine. Cells were split at a ratio of 1:10 every 2-3 days by trypsinization and resuspended in fresh medium in a new flask. Cells were harvested for experiments in the same way at 70-90% confluency.

CD1-Nu/Nu female mice, ~4-6 weeks old were obtained from Charles River Laboratories. Mice were housed 5 to a cage in a micro-isolator room in the Department of Animal Laboratory Research of New York State University (SUNY) at Stony Brook. Light-dark cycles were 12 h each daily, with light from 7 a.m. to 7 p.m. Food (Purina Rodent Chow) and water (distilled sterile-filtered water, pH 7) were provided ad libitum. Protocols and procedures were according to the rules of and approved by the SUNY Institutional Animal Care and Use Committee (IACUC).

An acclimation period of 7 days was allowed between the arrival of the animal at the study site before tumor inoculation and experimentation. Mice were inoculated subcutaneously (SC) in the right flank with $2×10^6$ human H460 NSCLC or BxPC3 pancreatic cancer cells that were suspended in 0.1 mL of Dulbeco's Phosphate Buffered Salt (PBS) solution using a 1 cc syringe with a 27-⅝ gauge needle. Tumor dimensions (length and width) were measured daily before, during and after treatment (using Vernier calipers) and the tumor volume was calculated using the prolate ellipsoid formula: (length×width$^2$)/2. Treatment with test or control articles began 8 days post tumor cell implantation when the tumor was approximately 300 mm$^3$.

Oral dosing of 6,8-bis(benzylsulfanyl)octanoic acid was at 100 mg/kg with 11 animals per group. 100 mg of 6,8-bis(benzylsulfanyl)octanoic acid was suspended in a small volume 0.01-0.05N NaOH in 5% dextrose and titrated to pH 7.0 with 4% Glacial Acetic Acid to 50 mg/mL. Prior to administration the suspension was diluted with 5% dextrose to 12.5 mg/mL so that the animals received 100 mg/kg with a dose volume of about 0.2 mL delivered by gastric gavage. Post tumor cell implantation, mice were treated on day 8, day 15, day 22, and day 29.

A similar study was conducted in CD-1 nude mice (n=9) inoculated with $2×10^6$ BxPC-3 cells. The study was initiated when tumors reached an average size of 150 mm$^3$ (day 0) and CPI-613 was administered at an oral dose of 100 mg/week for 4 weeks. A comparator arm (n=9) was conducted with IP treatment at a weekly dose of 25 mg/kg.

Figure 2:
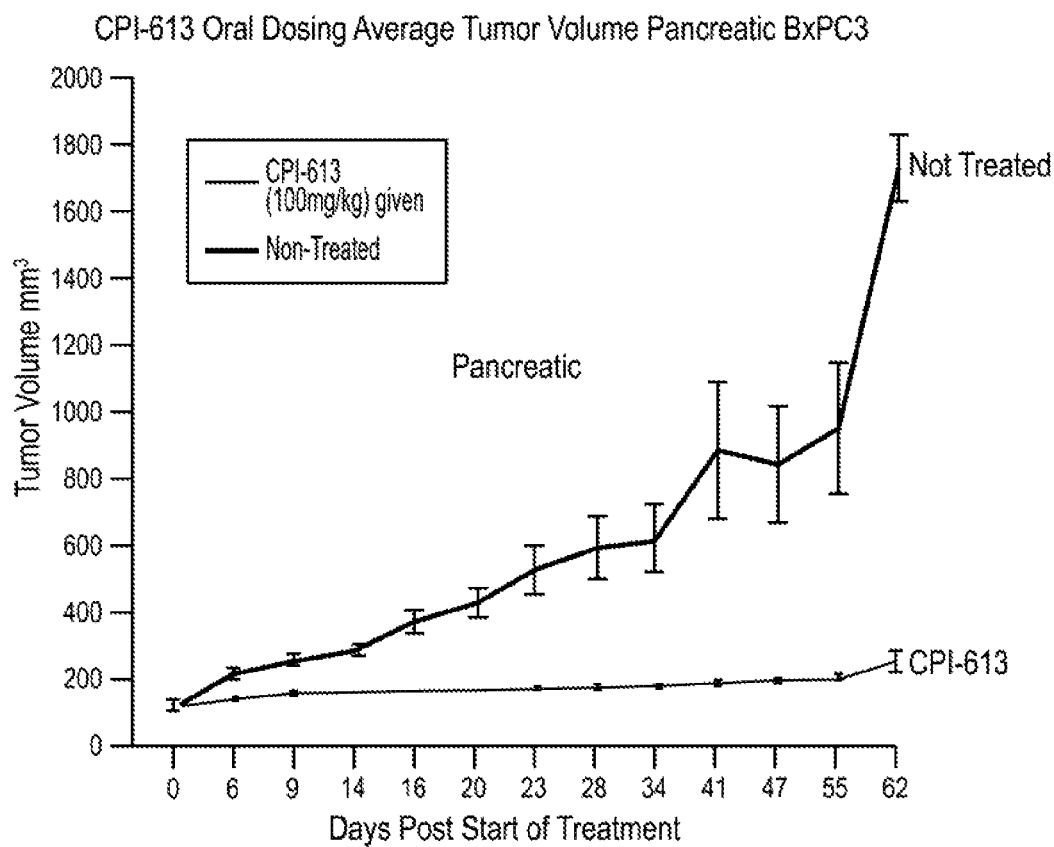
FIG. 2 depicts the anti-tumor efficacy of oral 6,8-bis(benzylsulfanyl)octanoic acid in human pancreatic cancer xenografts in mice.
Figure 2:
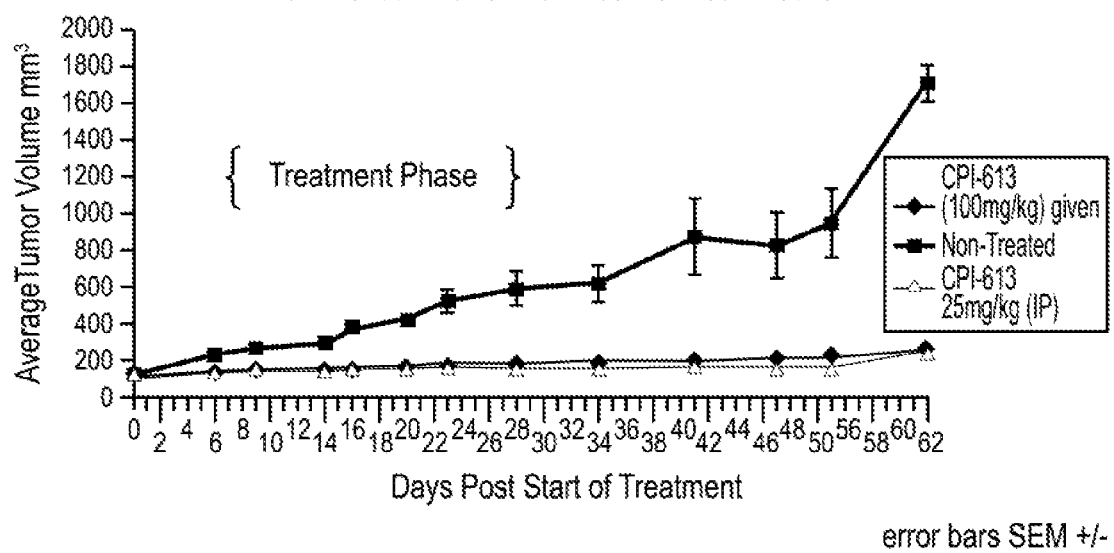

The results are presented in FIGS. 1 and 2. It is evident that the tumors in the mice treated with 6,8-bis(benzylsulfanyl)octanoic acid grew much more slowly than those in mice treated with 5% dextrose or untreated. The effect was especially pronounced in BxPC3 tumors. This example demonstrates that 6,8-bis(benzylsulfanyl)octanoic acid is effective to treat cancer when administered orally.

Example 3—Spray Dried Dispersion Oral Formulation of 6,8-Bis(benzylsulfanyl)octanoic Acid Solid amorphous dispersion formulations of 6,8-bis(benzylsulfanyl)octanoic acid (API) were prepared by mixing the API 1:4 with one of the following polymers: Eudragit L100, poly(vinylpyrrolidone) viscosity grade K30 (PVP K30), hydroxypropyl methyl cellulose (HPMC), cellulose acetate phthalate (CAP), or hydroxypropyl methylcellulose acetate succinate (HPMCAS-M), and spray drying from methanol or acetone using a small-scale Bend Lab Dryer with 35 kg/hr drying gas flow rate capacity (BLD-35). Conditions, yields, and residual solvent levels of two representative spray dried dispersion (SDD) formulations (75 g each) are presented in the following table.

| Formulation | 20% API: Eudragit L100 | 20% API: HPMCAS-M |
| --- | --- | --- |
| Spray Solution | 5% solids in methanol | 5% solids in acetone |
| Outlet Temp | 45° C. | 35° C. |
| Solution Feed Rate | 35 g/min | |
| Drying Gas Flow Rate | 475-500 g/min | |
| Atomization Pressure | 120 psi | |
| Nozzle | Schlick 2.0 pressure swirl atomizer | |
| Secondary Drying | 20 hr at 30° C. | |
| Dry Yield (%) | 94 | 96 |
| Residual Solvent (%) (Wet SDD) | 4.21 ± 0.02 (MeOH) | 1.01 ± 0.00 (Acetone) |
| Residual Solvent (%) (Tray-Dried Material) | <LOQ | <LOQ |
| API content by HPLC | 201 ± 1.1 mg/g | 198 ± 0.2 mg/g |

Scanning electron microscopy (SEM) was used to qualitatively determine particle morphology of the two SDD formulations, and to study if any degree of fusion or crystallinity was visually present. Particles show collapsed sphere morphology with no crystallization or fusion noted.

Figure 3:
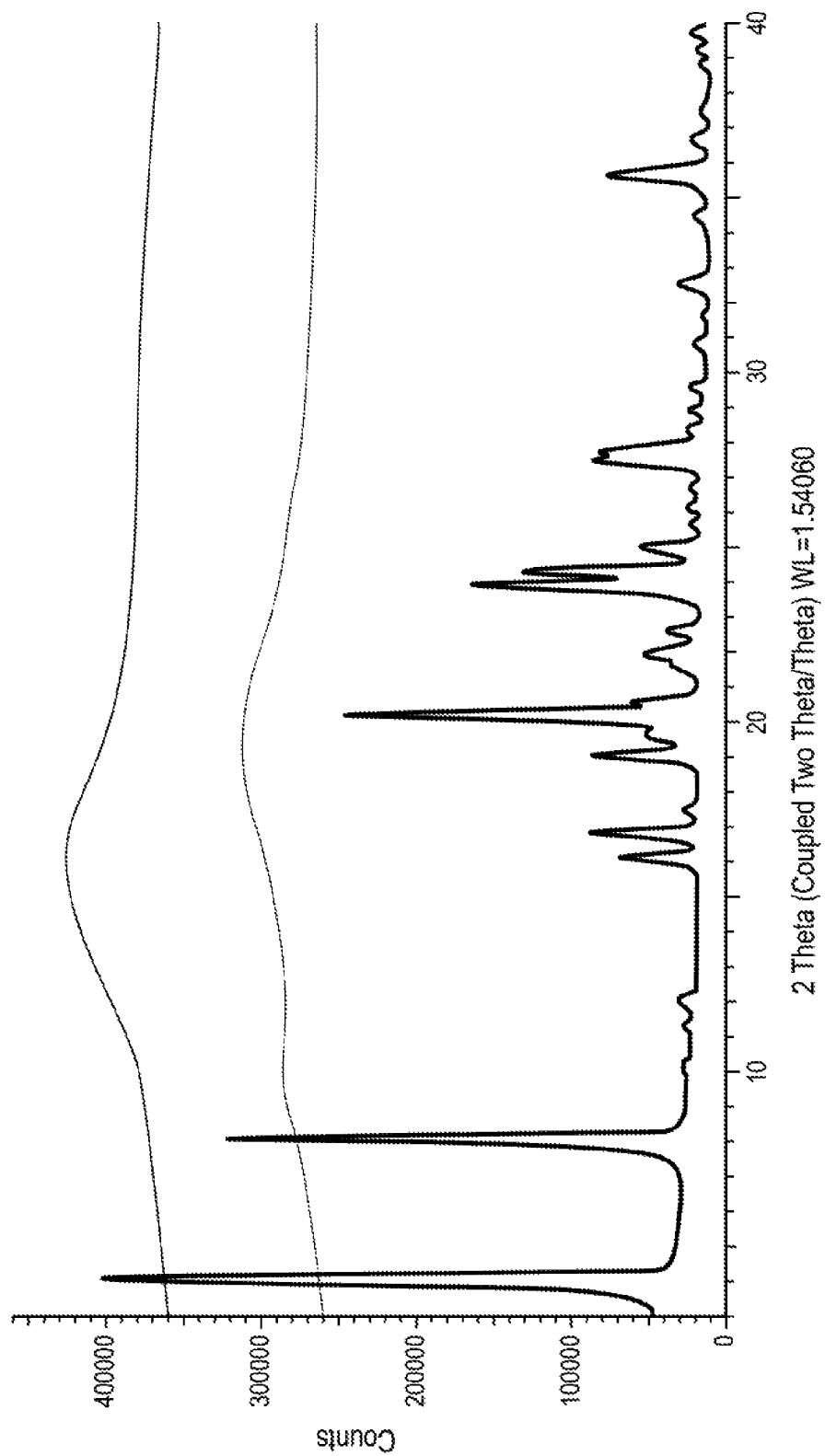
FIG. 3 presents X-ray powder diffraction patterns of solid amorphous dispersion formulations of 6,8-bis(benzylsulfanyl)octanoic acid with either Eudragit L100 or hydroxypropyl methylcellulose acetate succinate (HPMCAS-M) (top and middle diffraction patterns, respectively), and crystalline 6,8-bis(benzylsulfanyl)octanoic acid (bottom diffraction pattern).

X-ray diffraction is typically sensitive to the presence of crystalline material with an LOD of about 1% of the sample mass. No crystallinity was detected by PXRD for either SDD formulation. Diffractograms in comparison to crystalline 6,8-bis(benzylsulfanyl)octanoic acid API can be found in FIG. 3, wherein the top diffractogram is the Eudragit L100 formulation, the middle diffractogram is the HPMCAS-M formulation, and the bottom diffractogram is crystalline 6,8-bis(benzylsulfanyl)octanoic acid.

Example 4—Emulsion Oral Formulations of 6,8-Bis(benzylsulfanyl)octanoic Acid Monolaurin (131 mg) and 6,8-bis(benzylsulfanyl)octanoic acid (93 mg) were warmed to 50° C. in polysorbate-80 (2.5 mL) in a round bottomed flask equipped with a magnetic stir bar. After complete dissolution to a clear solution, water (7.5 mL) was added with vigorous stirring at 50° C. to provide an emulsion.

6,8-bis(benzylsulfanyl)octanoic acid (312 mg) was combined with polysorbate 80 (6.25 g), soybean oil (1.25 g), and a lipid mix (100 mg) comprising cholesterol (14 g), cholesteryl acetate (14 g), cholesteryl benzoate (14 g), monolaurin (25.4 g), and monopalmitin (32.6 g), and the mixture heated to 50° C. until the solids dissolved (30 min). Dextrose (11.25 g) was dissolved in 236 mL of water, and the resulting aqueous dextrose solution was added to the oil solution above. The resulting two phase mixture was stirred for 30 min at rt, then vacuum filtered through a 0.22 um filter.

Example 5—Liquid Formulations of 6,8-Bis(benzylsulfanyl)octanoic Acid

A 6,8-bis(benzylsulfanyl)octanoic acid solution was prepared by the steps of (a) providing a 50 mg/mL solution of 6,8-bis(benzylsulfanyl)octanoic acid in 1 M aqueous triethanolamine, and (b) diluting the 50 mg/mL solution with 5% aqueous dextrose to a concentration of 5 mg/mL. The resulting 5 mg/mL solution is identified as "5A" in Example 6 below.

A suspension vehicle was prepared by the steps of: (a) combining tris buffer (48 mg) and HPMCAS-HF (20 mg) in 14 mL of distilled water, (b) adjusting the pH to 7.4 with dilute sodium hydroxide to dissolve the HPMCAS-HF, (c) heating the resulting solution to approximately 90° C., (d) adding Methocel A4M Premium (100 mg) to the hot solution, (e) stirring the mixture vigorously to suspend the undissolved Methocel A4M, (f) cooling and stirring the mixture with an ice bath until the Methocel A4M dissolves (approximately 10 minutes), (g) diluting the solution with distilled/deionized water to bring the total volume to 20 mL, and (h) adjusting the pH to 7.4 with dilute acetic acid or dilute sodium hydroxide to provide the suspension vehicle.

Suspensions of the spray-dried formulations of Example 3 were prepared by adding 400 mg of the respective SDD formulation to a mortar, slowly adding 4 mL of the suspension vehicle (mixing thoroughly with a pestle after each small addition to uniformly disperse), and then transferring to a flask and stirring for one minute prior to administration. The resulting suspension of the Eudragit L100 SDD formulation (20 mg/mL 6,8-bis(benzylsulfanyl)octanoic acid) is identified as "5B" in Example 6 below. The resulting suspension of the HPMCAS-M SDD formulation (20 mg/mL 6,8-bis(benzylsulfanyl)octanoic acid) is identified as "5C" in Example 6 below.

In the same way, a 20 mg/mL suspension of 6,8-bis(benzylsulfanyl)octanoic acid was prepared by adding 80 mg 6,8-bis(benzylsulfanyl)octanoic acid to a mortar, slowly adding 4 mL of the suspension vehicle (mixing thoroughly with a pestle after each small addition to uniformly disperse), and then transferring to a flask and stirring for one minute prior to administration. The resulting suspension of 6,8-bis(benzylsulfanyl)octanoic acid is identified as "5D" in Example 6 below.

A solution of 6,8-bis(benzylsulfanyl)octanoic acid was prepared by dissolving SOLUTOL® (polyoxyl 15 hydroxystearate; KOLLIPHOR® HS 15) (3 grams) in distilled water (7 mL) to form a 30% solution, adding 6,8-bis(benzylsulfanyl)octanoic acid (50 mg) to 5 mL of the 30% solution, vortexing for 1 minute, and then sonicating for 45 minutes to provide a clear colorless solution (10 mg/mL; pH 7). The resulting solution is identified as "5E" in Example 6 below.

Example 6—Oral Bioavailability of 6,8-Bis(benzylsulfanyl)octanoic Acid

Six groups of 16 BALB/c nude mice (8 males and 8 females) per group were administered 6,8-bis(benzylsulfanyl)octanoic acid in six different ways: (1) 5 μL/g IV injection (tail vein) of the triethanolamine/dextrose aqueous solution of Example 5 (25 mg/kg; 5 mL/kg; Ex. 5A); (2) 5 μL/g IP injection of the triethanolamine/dextrose aqueous solution of Example 5 (25 mg/kg; 5 mL/kg; 5A); (3) 5 μL/g oral administration of the Eudragit L100 SDD suspension of Example 5 (100 mg/kg; 5 mL/kg; 5B); (4) 54/g oral administration of the HPMCAS-M SDD suspension of Example 5 (100 mg/kg; 5 mL/kg; 5C); (5) 5 μL/g oral administration of the 20 mg/mL 6,8-bis(benzylsulfanyl)octanoic acid suspension of Example 5 (100 mg/kg; 5 mL/kg; 5D); or (6) 10 μL/g oral administration of the 10 mg/mL SOLUTOL solution of Example 5 (100 mg/kg; 10 mL/kg; 5E). In each experiment, about 80 μL of blood was collected from one subgroup of 4 male and 4 female mice at 0.083, 1, 4, and 24 hours after dosing, and from the other subgroup of 4 male and 4 female mice at 0.5, 2, and 8 hours. Plasma from the collected blood samples was analyzed by LC-MS/MS for the presence of 6,8-bis(benzylsulfanyl)octanoic acid.

| Formulation | Route | Mice (n) | Dose (mg/kg) | Bioavailability (%) | AUC Last (uM * hr) | Cmax (uM) | Tmax (hr) | T 1/2 (hr) |
|---|---|---|---|---|---|---|---|---|
| 5A (TEA/dextrose) | IV | 16 | 25 | — | 36 | 92 | 0.08 | 2.0 |
| 5A (TEA/dextrose) | IP | 16 | 25 | 83 | 29 | 103 | 0.08 | 3.9 |
| 5B (Eudragit SDD) | PO | 16 | 100 | 44 | 61 | 94 | 0.08 | 2.0 |
| 5C (HPMCAS-M SDD) | PO | 16 | 100 | 43 | 60 | 69 | 0.08 | 1.1 |
| 5D (CPI-613) | PO | 16 | 100 | 57 | 82 | 82 | 0.50 | 3.7 |
| 5E (Solutol) | PO | 16 | 100 | 127 | 175 | 229 | 0.08 | 4.4 |

This example demonstrates that 6,8-bis(benzylsulfanyl)octanoic acid is orally bioavailable.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A method for treating pancreatic cancer, comprising administering to a patient in need thereof a therapeutically effective amount of (i) a first therapeutic agent comprising 6,8-bis(benzylsulfanyl)octanoic acid or a pharmaceutically acceptable salt thereof, (ii) a second therapeutic agent comprising gemcitabine or a pharmaceutically acceptable salt thereof, and (iii) a third therapeutic agent comprising nab-paclitaxel, in order to treat the pancreatic cancer, wherein the first therapeutic agent, the second therapeutic agent, and the third therapeutic agent are administered to the patient on days 1, 8, and 15 of a twenty-eight day cycle, and the first therapeutic agent is administered to the patient at a dosage of about 500 mg/m$^2$, about 1000 mg/m$^2$, or about 1500 mg/m$^2$ on any day the first therapeutic agent is administered to the patient.

2. The method of claim 1, wherein the pancreatic cancer is metastatic pancreatic cancer.

3. The method of claim 1, wherein the pancreatic cancer is locally advanced.

4. The method of claim 1, wherein the first therapeutic agent is administered no more frequently than once per any seven day period.

5. The method of claim 4, wherein the second therapeutic agent is administered to the patient no more frequently than once per any seven day period.

6. The method of claim 5, wherein the third therapeutic agent is administered to the patient no more frequently than once per any seven day period.

7. The method of claim 1, wherein the second therapeutic agent is administered to the patient at a dosage ranging from about 650 mg/m$^2$ to about 800 mg/m$^2$ on any day the second therapeutic agent is administered to the patient.

8. The method of claim 7, wherein the third therapeutic agent is administered to the patient at a dosage ranging from about 80 mg/m$^2$ to about 100 mg/m$^2$ on any day the third therapeutic agent is administered to the patient.

9. The method of claim 6, wherein the second therapeutic agent is administered to the patient at a dosage ranging from about 650 mg/m$^2$ to about 800 mg/m$^2$ on any day the second therapeutic agent is administered to the patient.

10. The method of claim 9, wherein the third therapeutic agent is administered to the patient at a dosage ranging from about 80 mg/m$^2$ to about 100 mg/m$^2$ on any day the third therapeutic agent is administered to the patient.

* * * * *